(12) United States Patent
Chin et al.

(10) Patent No.: US 12,084,641 B2
(45) Date of Patent: Sep. 10, 2024

(54) SYSTEM FOR PRODUCING CULTIVATED MEATS, TISSUES AND ASSOCIATED PRODUCTS FROM CELLS

(71) Applicant: Avant Meats Company Limited, Hong Kong (CN)

(72) Inventors: Po San Mario Chin, Hong Kong (CN); Kai Yi Carrie Chan, Hong Kong (CN); Chuen Wai Li, Hong Kong (CN); Tim Spitters, Hong Kong (CN)

(73) Assignee: AVANT MEATS COMPANY LIMITED, Hong Kong (CN)

( * ) Notice: Subject to any disclaimer, the term of this patent is extended or adjusted under 35 U.S.C. 154(b) by 0 days.

(21) Appl. No.: 17/395,452

(22) Filed: Aug. 5, 2021

(65) Prior Publication Data

US 2022/0025310 A1 Jan. 27, 2022

Related U.S. Application Data

(63) Continuation of application No. PCT/IB2020/061257, filed on Nov. 30, 2020.

(Continued)

(51) Int. Cl.
  *C12M 1/00* (2006.01)
  *A23L 13/00* (2016.01)
  (Continued)

(52) U.S. Cl.
  CPC ............. *C12M 21/08* (2013.01); *A23L 13/00* (2016.08); *A23L 17/00* (2016.08); *C12M 29/04* (2013.01); *C12N 5/0652* (2013.01); *C12N 5/0656* (2013.01); *C12N 5/0662* (2013.01); *C12N 5/0679* (2013.01); *C12N 5/0696* (2013.01); *C12N 5/0697* (2013.01);
  (Continued)

(58) Field of Classification Search
  None
  See application file for complete search history.

(56) References Cited

U.S. PATENT DOCUMENTS

| 3,418,208 A | 12/1968 | Coty |
| 6,126,935 A | 10/2000 | Van Bossuyt |

(Continued)

FOREIGN PATENT DOCUMENTS

| CN | 1720064 A | 1/2006 |
| CN | 103992385 | 8/2014 |

(Continued)

OTHER PUBLICATIONS

China National Intellectual Property Administration, International Search Report, Feb. 25, 2021, 4 pages.

(Continued)

*Primary Examiner* — Liban M Hassan
(74) *Attorney, Agent, or Firm* — Loeb & Loeb LLP

(57) ABSTRACT

A cell/tissue culture system comprising at least one bioreactor configured to hold at least one type of cell to cultivate tissue, a dialysis unit comprising a dialysis membrane, a fresh medium unit, and a waste removal unit configured to remove metabolic waste from dialysate, wherein the metabolic waste comprises ammonia and lactate, and wherein the waste removal unit comprises biocatalysts or enzymes configured to breakdown lactate and generate carbon sources that promote cell growth.

9 Claims, 12 Drawing Sheets

Related U.S. Application Data

(60) Provisional application No. 62/942,568, filed on Dec. 2, 2019.

(51) Int. Cl.

| | | |
|---|---|---|
| A23L 17/00 | (2016.01) | |
| C12M 3/00 | (2006.01) | |
| C12N 5/071 | (2010.01) | |
| C12N 5/074 | (2010.01) | |
| C12N 5/077 | (2010.01) | |
| C12N 5/0775 | (2010.01) | |
| C12N 15/113 | (2010.01) | |

(52) U.S. Cl.
CPC ........ *C12N 15/113* (2013.01); *A23V 2002/00* (2013.01); *C12N 2310/141* (2013.01); *C12N 2501/105* (2013.01); *C12N 2501/11* (2013.01); *C12N 2501/115* (2013.01); *C12N 2501/2306* (2013.01); *C12N 2501/2311* (2013.01); *C12N 2501/33* (2013.01); *C12N 2501/998* (2013.01); *C12N 2510/00* (2013.01); *C12N 2513/00* (2013.01); *C12N 2531/00* (2013.01); *C12N 2533/74* (2013.01)

(56) References Cited

U.S. PATENT DOCUMENTS

| | | | |
|---|---|---|---|
| 11,306,342 B2 | 4/2022 | Chin | |
| 2007/0122904 A1 | 5/2007 | Nordon | |
| 2010/0197007 A1* | 8/2010 | Cailleret | C12N 5/0606 435/325 |
| 2011/0091604 A1* | 4/2011 | Miller | C12M 29/10 426/574 |
| 2013/0323708 A1 | 12/2013 | Yarmush | |
| 2014/0206056 A1* | 7/2014 | Hazewinkel | C02F 3/286 435/167 |
| 2015/0225750 A1* | 8/2015 | Huo | C12Y 104/01009 435/160 |
| 2019/0247409 A1* | 8/2019 | Welman | C12N 9/2471 |
| 2019/0376026 A1* | 12/2019 | Forgacs | C12N 5/0697 |
| 2020/0080050 A1* | 3/2020 | Nahmias | C12N 5/0062 |
| 2021/0246480 A1 | 8/2021 | Chin | |

FOREIGN PATENT DOCUMENTS

| | | |
|---|---|---|
| CN | 104109705 A | 10/2014 |
| CN | 104313098 | 1/2015 |
| CN | 105219827 | 1/2016 |
| CN | 106749634 A | 5/2017 |
| CN | 106805252 A | 6/2017 |
| CN | 107400633 A | 11/2017 |
| CN | 109714962 | 5/2019 |
| CN | 110117527 | 8/2019 |
| CN | 110201000 A | 9/2019 |
| WO | 9310217 | 5/1993 |
| WO | 2007139742 | 12/2007 |
| WO | 2008124569 | 10/2008 |
| WO | 2011103359 | 8/2011 |
| WO | 2015066377 | 5/2015 |
| WO | 2016128361 | 8/2016 |
| WO | 2018011805 A2 | 1/2018 |
| WO | 2018011805 A3 | 2/2018 |
| WO | 2018011805 A9 | 4/2018 |
| WO | 2018227016 | 12/2018 |

OTHER PUBLICATIONS

Gene News, CELLine, A double-compartment cell cell culture device, No. 2, Dec. 31, 2007, 2 pages.
China National Intellectual Property Administration, Written Opinion, Feb. 22, 2021, 3 pages.
Chen et al., "Preparation and functional evaluation of collagen oligopeptide-rich hydrolysate from fish skin with the serine collagenolytic protease from *Pseudoalteromonas* sp. SM9913," Nature, Scientific Reports, Nov. 16, 2017, pp. 1-13. (Year: 2017).
CN 104109705 Machine translation, Oct. 22, 2014, pp. 1-13. (Year: 2014).
Giron-Calle et al., "Chickpea protein hydrolysate as a substitute for serum in cell culture," Cytotechnology, 2008, 57: 263-272. (Year : 2008).
International Search Report and Written Opinion for App. No. PCT/IB2020/060727, dated Feb. 23, 2021, 6 pages.
Jiang et al., Therapeutic Effect of Polysaccharide of Large Yellow Croaker Swim Bladder on Lupus Nephritis of Mice, Nutrients, 2014, 6: 1223-1235. (Year: 2014).
Liu et al., "Potential Application of Hydrolyzed Fish Collagen for Inducing the Multidirection of Rat Bone Marrow Mesenchymal Stem Cells," BioMacromolecules, Dec. 23, 2013, pp. 436-443. (Year: 2013).
Office Action dated Oct. 7, 2021 for U.S. Appl. No. 17/243,493 (pp. 1-21).
Office Action (Notice of Allowance and Fees Due (PTOL-85)) dated Mar. 2, 2022 for U.S. Appl. No. 17/243,493 (pp. 1-11).
Falkenberg, F.W. ; Hengelage, T. ; Krane, M. ; Bartels, I. ; Albrecht, A. ; Holtmeier, N. ; Wuthrich, M., "A simple and inexpensive high density dialysis tubing cell culture system for the in vitro production of monoclonal antibodies in high concentration", Journal of Immunological Methods, Elsevier Science Publishers B.V.,Amsterdam., NL, NL, (Oct. 15, 1993), vol. 165, No. 2, doi: 10.1016/0022-1759(93)90345-8, ISSN 0022-1759, pp. 193-206, XP023656465.
Herkenhoff Marcos E., Oliveira Arthur C., Nachtigall Pedro G., Costa Juliana M., Campos Vinicius F., Hilsdorf Alexandre W. S., Pinhal Danillo, "Fishing Into the MicroRNA Transcriptome", Frontiers in Genetics, (Oct. 1, 2018), vol. 9, doi:10.3389/fgene.2018.00088, p. 88, XP055819312.
Jafarinejad-Farsangi Saeideh, Gharibdoost Farhad, Farazmand Ali, Kavosi Hoda, Jamshidi Ahmadreza, Karimizadeh Elham, Noorbakhsh Farshid, Mahmoudi Mahdi, "MicroRNA-21 and microRNA-29a modulate the expression of collagen in dermal fibroblasts of patients with systemic sclerosis", Autoimmunity, Informa Healthcare, GB, GB, (Apr. 3, 2019), vol. 52, No. 3, doi: 10.1080/08916934.2019.1621856, ISSN 0891-6934, pp. 108-116, XP055819251.
Kumar Pal Gaurav, Thadathil Nidheesh, Karadka Govindaraju,Jyoti,Puthanveetil Velappan Suresh, "Enzymatic extraction and characterisation of a thermostable collagen from swim bladder of rohu(*Labeo rohita*)", Journal of the Science of Food and Agriculture, (Jul. 6, 2016), vol. 97, No. 5, doi: 10.1002/jsfa.7884, pp. 1451-1458, XP055975370, Available online at https://onlinelibrary.wiley.com/doi/10.1002/jsfa.7884.
Li, Y.L.et al., "Research progress on collagen from fish swim bladders: a review.", Journal of Dalian Ocean University, (Feb. 29, 2020), vol. 35, No. 1, ISSN 2095-1388, pp. 31-38, XP009540161, Available online at https://xuebao.dlou.edu.cn/EN/Y2020/V35/11/31.
Luke A. Macqueen, Alver Charles G., Chantre Christophe O., Ahn Seungkuk, Cera Luca, Gonzalez Grant M., O'connor Blakely B., Drennan Daniel J., Peters Michael M., Motta Sarah E., Zimmerman John F., Parker Kevin Kit, "Muscle tissue engineering in fibrous gelatin: implications for meat analogs", npj Science of Food, (Dec. 1, 2019), vol. 3, No. 1, doi:10.1038/s41538-019-0054-8, XP055755653.
P Bama, Vijayalakshimi M, Jayasimman R, Kalaichelvan P T, Deccaraman M, Sankaranarayanan S, "Extractionofcollagenfromc atfish(*Tachysurusmaculatus*)BypepsinDigestionandpreparationandc haracterizationofcollagenchitosansheet", (Jun. 10, 2010), URL: https://www.researchgate.net/publication/287948097_Extraction_of_collagen_from_cat_fish_tachysurus_maculatus_by_pepsin_digestion_and_prep.
Proudfoot D., D.P. Parrott, D.E. Bowyer, "A dialysis culture system for the study of the production and modulation of growth-regulatory molecules: studies using the P388D1 macrophage cell line", Journal of Cell Science, (Jan. 1, 1995), vol. 108, pp. 379-386, XP055819302.
Sharma Shruti; Thind Sukhcharanjit Singh; Kaur Amarjeet, "In vitro meat production system: why and how?", Journal of Food Science and Technology, Springer (India) Private Ltd., India, India, (Jul. 31,

(56) References Cited

OTHER PUBLICATIONS

2015), vol. 52, No. 12, doi:10.1007/s13197-015-1972-3, ISSN 0022-1155, pp. 7599-7607, XP035965731.
Viernamese Office Action (including English translation) issued in App. No. VN1202203962, dated Aug. 25, 2022, 3 pages.
Vietnamese Office Action (including English translation) issued in App. No. VN1-2022-03728, dated Aug. 26, 2022, 4 pages.
Extended European Search Report issued in App. No. EP20895302, dated Mar. 1, 2024, 8 pages.
International Preliminary Report on Patentability issued in App. No. PCT/IB2022/053340, dated Oct. 10, 2023, 4 pages.
International Preliminary Report on Patentability issued in App. No. PCT/IB2022/053341, dated Feb. 6, 2024, 6 pages.
Zhao et al., " Anti-Fatigue Effect by Peptide Fraction from Protein Hydrolysate of Croceine Croaker (Pseudosciaena crocea) Swim Bladder through Inhibiting the Oxidative Reactions including DNA Damage" Marine Drugs., 14, 221; Doi:10.3390/md14120221. 2016. 18 pages.

\* cited by examiner

SYSTEM FOR PRODUCING CULTIVATED MEATS, TISSUES AND ASSOCIATED PRODUCTS FROM CELLS

CROSS REFERENCE TO RELATED APPLICATIONS

The present application claims priority to a PCT patent application PCT/IB2020/061257 filed on Nov. 30, 2020, which further claims priority to a provisional application Ser. No. 62/942,568, filed on Dec. 2, 2019, whose disclosures are incorporated by reference in their entirety herein.

TECHNICAL FIELD

Embodiments discussed herein generally relate to improved systems and methods for growing cell culture. Embodiments discussed herein also generally relate to the improved systems and methods for in vitro meat production and tissue constructions/engineering.

BACKGROUND

Animal meat is high in protein, and supplies all the amino acids needed to build the protein used to support body functions. Meat for consumption is traditionally obtained from animals or fish that are reared on farms. However, agriculture and aquaculture for producing animal meat require a large amount of energy and resources, and have a high carbon footprint. Meat produced by agriculture or aquaculture may pose a public health risk as the production processes may expose the meat to diseases, pollutants, and toxins. A number of concerns such as a growing population, increasing demand for meat, environmental concerns, limited land and water resources, biodiversity loss, and the negative perception associated with animal slaughter have led scientists to develop techniques to produce meat by alternative processes.

In vitro meat production is the process by which muscle tissue or organ tissue from animals is grown in laboratories using cell culture techniques to manufacture meat and meat products. As used herein, in vitro meat and meat products includes animal protein products as well as non-meat products including soluble forms and solid forms. While still in an early stage of development, in vitro meat and meat products may offer a number of advantages over traditional meat products such as health and environmental advantages, and benefits to animal welfare. It is a next-generation and emerging technology that operates as part of a wider field of cellular agriculture, or the production of agricultural products from cell cultures.

Cells for the production of in vitro meat may be cells (e.g., muscle cells, somatic cells, stem cells, etc.) taken from animal biopsies, which may then be grown separately from the animal in culture media in a bioreactor or other type of sterile, controlled environment. The cells may grow into a semi-solid or solid form mimicking an animal organ by attaching to an edible three-dimensional scaffold that is placed in the bioreactor. The starter cells may be primary cells directly obtained from the animal's tissues, or continuous cell lines. If grown under the right conditions in appropriate culture media, primary cells will grow and proliferate, but only a finite number of times that is related to the telomere length at the end of the cell's DNA. Continuous cell lines, on the other hand, can be cultured in vitro over an extended period. Cell biology research has established procedures on how to convert primary cells into immortal continuous cell lines. Primary cells may be transformed into continuous cell lines using viral oncogenes, chemical treatments, or overexpression of telomerase reverse transcriptase to prevent the telomeres from shortening.

The culture media may contain components necessary for cell proliferation such as amino acids, salts, vitamins, growth factors, and buffering systems to control pH. Current methods add fetal bovine serum (FBS) to the media before use as it provides vital macromolecules, growth factors, and immune molecules. However, FBS is derived from unborn calves and, therefore, is incompatible with the objective of being free from animal products. Growing the cells in an animal component-free medium is an important factor considered by scientists involved in in vitro meat production research. Some growth factors may be derived from human, animal or recombinant sources.

Commodity meat types beef, pork and poultry meats have a complex tissue organization involving multiple cell types that are difficult and costly to produce. The cells of the current in vitro meat usually attach/adhere to a food-grade biocompatible scaffold, which is made from ingredients sourced from plants. As a result, the cultivated meat products are a combination of animal cells with the edible scaffold. Such meat products are homogeneous in structure compared with conventional meat since it is merely a combination of animal cells mixed with edible form-giving filler materials sourced from plants. The current in vitro meat products cannot satisfy consumers due to the difficulty of mimicking the taste and texture of conventional meats. It also lacks complex tissue organization involving multiple cell types. There is a need to improve the structure, texture and tissue organization of in vitro meat as those from conventional meat in order to meet consumers' demands and gain long-term support from the general public.

In addition, in the production of in vitro meats or the clinical applications of regenerative medicine/tissue engineering/tissue construction, it is critical to harvest a sufficient cell number. In the application of production of in vitro meat, 1 kg of protein contains approximately $8 \times 10^{12}$ muscle cells. In the application of regenerative medicine, approximately $10^{10}$ to $10^{12}$ cells per treatment are required for most applications. For example, $1 \times 10^9$ to $2 \times 10^9$ cardiomyocytes would be required to replace damaged cardiac tissue in adults. Treating hepatic failure would require a cell number of $10^{10}$ hepatocytes.

The current cell culture approach seeds cells on the 2D culture surface of culture vessels in the presence of a culture medium. In general, the culture medium contains glucose, vitamins, inorganic salts, amino acids and other nutrients. As the cells grow, nutrients are gradually depleted and metabolic wastes accumulate. Therefore, the culture medium is replaced every 2 to 3 days to replenish nutrients and remove wastes. There are several problems with this cell culture approach. Firstly, cells grow in suboptimal conditions between medium replacements. Particularly if the cells are highly proliferative and have a high metabolic rate, cells consume nutrients such as glucose and accumulate waste such as lactate and ammonia in a short time. An elevated level of metabolic wastes or growth inhibitors can inhibit cell growth. This hinders cells from growing at an optimal rate before the next round of medium replacement. Secondly, changing culture medium wastes nutrients and growth factors; and increases production costs. There are still nutrients in the spent culture medium when it is replaced. Particularly, growth factors in the spent culture medium, either from serum supplements or secreted by cells, are removed during medium replacement. This increases the use of serum supplements, which contributes to a significant portion of medium cost and production cost. Thirdly, the medium needs to be changed manually and this increases production costs and the chance of contamination in large-scale manufacturing.

Further, it is observed that ammonium or lactate accumulation in the culture medium can inhibit cell growth and cell productivity. Multiple approaches were proposed to reduce ammonia accumulation in the culture. These include replacement of glucose and glutamine with alternative sugars and amino acids, using real-time feedback control of glucose or glutamine at optimal levels using glucose and glutamate sensor and reduce incubations temperature. However, none of these methods are universally effective across cell lines and bioprocesses at reducing ammonia production while having no negative impact on cell growth.

Yet, multiple approaches were proposed to reduce lactate accumulation in the culture. These include replacement of glucose and glutamine with alternative sugars and amino acids, using real-time feedback control of glucose and glutamine with alternative sugars and amino acids, using real-time feedback control of glucose or glutamine at optimal levels using glucose and glutamate sensor, supplement the culture with copper ions, reduce incubations temperature and reduce pH in the culture. However, none of these methods are universally effective across cell lines and bioprocesses at reducing lactate production while having no negative impact on cell growth.

None of the existing bioreactors can solve the foregoing issues and achieve the foregoing requirements in one go. Particularly, the existing stirred-suspension bioreactors are not suitable for the production of in vitro meat with complex tissue organization involving multiple cell types as they cannot support high cell density cell growth. Cells in such stirred-suspension bioreactors are in suspension and cell density in such bioreactors is limited due to shear stress. Most importantly, there is no component in such bioreactors to allow cells to deposit onto the extracellular matrix (ELM) and/form tissue. The products from such stirred-suspension bioreactors cannot provide the structure, texture and tissue organization as those from conventional meat.

Organ-on-a-chip is another cell culturing technique, yet, is not suitable for the production of in vitro meat as it cannot be used in large-scale production.

The production cost for the production of in vitro meat using existing stirred-suspension bioreactors and organ-on-a-chip is not economical due to the failure to retain specific metabolites and discard growth inhibitors during cell growth and manual processes.

Last but not least, the existing stirred-suspension bioreactors or organ-on-a-chip are not environment-friendly approaches to culture cells. There is no treatment of the waste produced from cell culturing. It would create an environmental issue if it is under large-scale production.

In summary, none of the existing bioreactors allow economic production of in vitro meat with structure, texture and tissue organization that are similar to the conventional meat at a scale commercially viable for production of in vitro meat.

SUMMARY

The embodiments of the present disclosure apply methods for in vitro meat production for human consumption that provides a solution to the above challenges.

In the light of the foregoing background, in one aspect, it is an objective of the present invention to provide an alternative bioreactor system and method to produce consumable in vitro meats, and/or tissues engineering/regenerative medicine/tissue construction applications (1) with improved structure, texture and tissue organization that are similar to the conventional meats, (2) economically, and (3) environmentally friendly approach (e.g. reduced waste). The bioreactor system and method of the present invention address all the problems as mentioned in the foregoing background in one single setup. The bioreactor system and method of the present invention employ fed-batch which can remove waste and replenish nutrients in the bioreactor while minimizing contamination risks, labor requirements and use of culture medium. The present invention supports high cell density growth compared to batch process and traditional perfusion technique as it continuously replenishes nutrients, removes accumulated growth inhibitors and reduces shear stress acting on the cells. The bioreactor system and method of the present invention are highly suitable for economically in vitro meat production cells with improved structure, texture and tissue organization that are similar to the conventional meat. It is also suitable for the production of in vitro meat with complex tissue organization involving multiple cell types. It is also an objective of the present invention to provide a system that maintains an optimal culture condition, stable level of nutrients and/or a minimum level of growth inhibitors for in vitro meat production. Yet another objective of the present invention is to provide a large-scale in vitro meat production system that can automatically replenish nutrients and remove growth inhibitors produced by the cells while retaining unused growth factors to enhance productivity and reduce cost.

Another objective of the present invention is to provide a method for in vitro meat production using the in vitro meat production system. Furthermore, an objective of the present invention is to provide a method for tissue engineering/construction using this system. Finally, an objective of the present invention is to provide a method for expanding cells to a clinically relevant number for regenerative medicine applications.

Yet another objective of the present invention is to provide an alternative method for removing the metabolic waste (e.g. ammonia and lactate) from the culture medium, thus lower the cost of and increasing productivity of the in vitro meat production.

The present invention further provides the following advantages: (1) keeping nutrients such as glucose at an optimal level and waste such as ammonia and lactate at a minimal level in the culture medium for optimal cell viability and cell growth; (2) retaining growth factors secreted by cells and reducing the use of animal-derived serum in the culture medium; (3) promoting cell growth, differentiation, and extracellular matrix deposition by converting lactate (metabolic waste) into carbon sources that cells can use; (4) providing an extracellular matrix and reduced shear stress environment that resemble an in-vivo environment for cells to grow; and (5) providing a reliable holder for holding the scaffold or the extracellular matrix. Growth factors are expensive, therefore the present invention helps lower the cost and optimizes medium use by retaining the growth factors in the culture medium while removing and converting the wastes.

As it will be discussed in more detail below, the present invention dramatically (1) reduces wastes discharged from the cell culturing system and (2) increases the cell mass production compared to the conventional technique.

According to one embodiment of the present disclosure, a system for in vitro meat production comprising a bioreactor configured to hold at least one type of cells to form tissue, a dialysis unit comprising a dialysis membrane configured to replenish nutrients to the cells and remove metabolic waste from the bioreactor to dialysate, a fresh medium unit connected to the dialysis unit and configured to supply the dialysate to the dialysis unit, and a waste removal unit connected to the fresh medium unit and configured to remove the metabolic waste from the dialysate, wherein the dialysate comprises nutrients for the cells, wherein the metabolic waste comprises ammonia and lactate, wherein the waste removal unit comprises a first biocatalyst configured to breakdown ammonia, wherein the waste removal unit comprises a second biocatalyst configured to breakdown lactate, wherein each of the bioreactors, the dialysis unit, the fresh medium unit and the water removal unit are detachably connected to the system.

The bioreactor may further include a platform for cells to grow three-dimensionally thereon, and a holder configured to receive and hold at least one platform, wherein the platform is an edible scaffold or extracellular matrix.

According to another embodiment of the present disclosure, a method for in vitro meat production including the steps of providing the system of the present invention, placing at least one type of cell into the bioreactor and producing tissue in the bioreactor, extracting at least ammonia and lactate from the bioreactor to the dialysate through the dialysis unit; generating fresh carbon source at the waste removal unit that promotes cell growth at the waste removal unit; and transferring such fresh carbon source from the dialysate to the bioreactor.

Embodiments disclosed herein apply systems and methods for in vitro meat production for human consumption and/or tissue engineering/tissue constructions/regenerative medicine applications that provide solutions to the above challenges.

BRIEF DESCRIPTION OF THE DRAWINGS

The disclosure may be better understood by reference to the detailed description when considered in connection with the accompanying drawings. The components in the figures are not necessarily to scale, emphasis instead being placed upon illustrating the principles of the disclosure.

DETAILED DESCRIPTION

Figure 1:
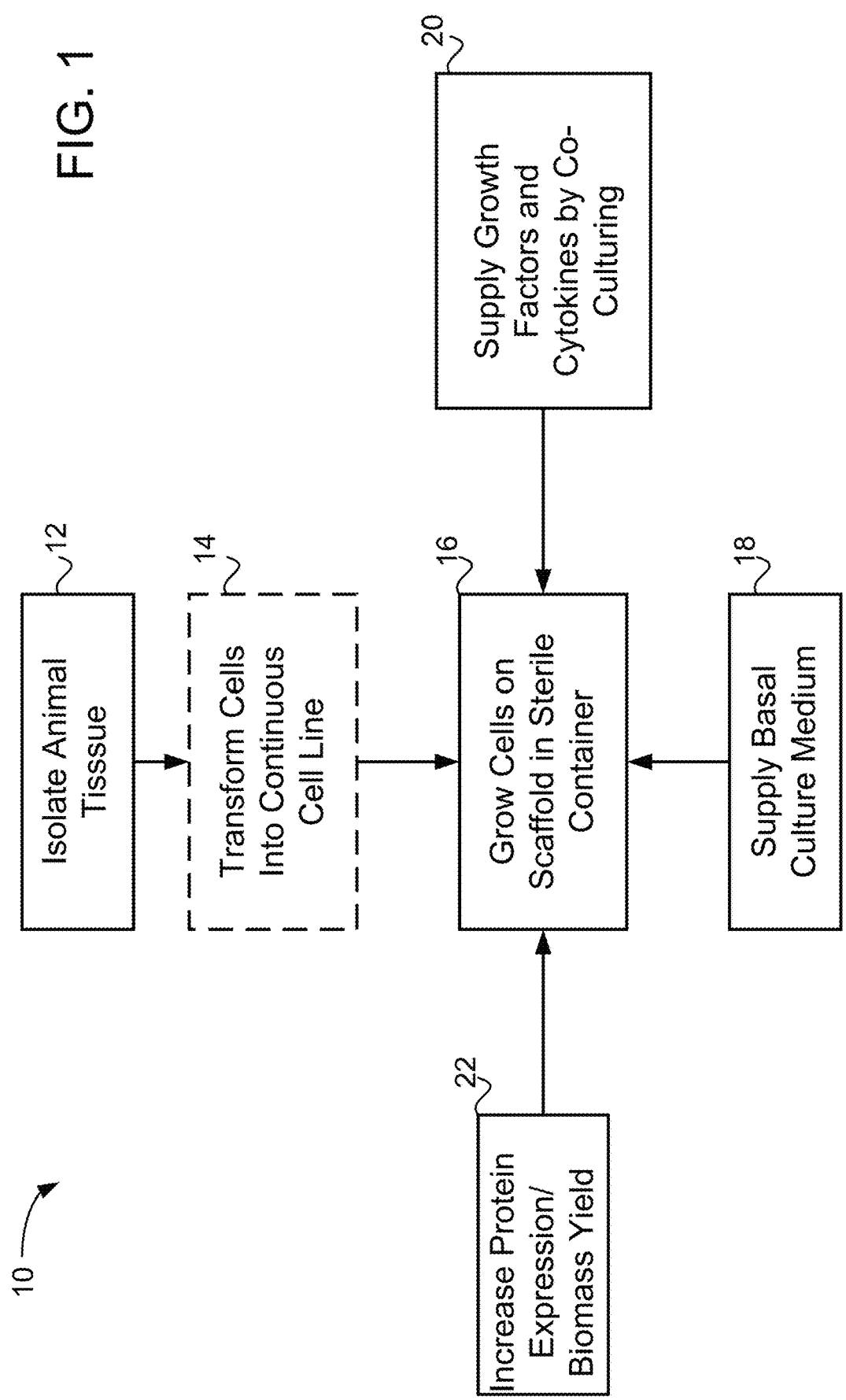
FIG. 1 is a flowchart of a method for in vitro meat production, according to one embodiment of the present disclosure.

As used herein, "in vitro meat production" refers to a cell-based meat production process or cell-based agriculture process in which tissues from animals and/or plants are grown in laboratories using cell culture techniques to manufacture meat and meat products. As used herein, "bioreactor", "cell culture unit" and "cell/tissue culture unit" are used interchangeably and refers to a bioreactor for in vitro meat production. Referring now to the drawings, and with specific reference to FIG. 1, a method 10 for in vitro meat production is shown.

At block 12, tissue from an animal or a plant is isolated. In one embodiment, the tissue is derived from bony fish of the class Osteichthyes including saltwater fish such as a grouper, sea bass, or yellow cocker. In other embodiments, other types of animal tissue, such as cow tissue, may be isolated. In some embodiments, block 12 may involve collecting organ tissue, such as a swim bladder, from a fish and making a cell suspension. Although the following description primarily describes tissues derived from fish sources, it will be understood that the concepts may be applied to tissues derived from other types of animal sources and/or plant sources to provide other types of in vitro meat and/or animal protein products, and vegetarian meat and/or protein products.

Many of the isolated cells are adult cells, and can be made to proliferate continuously using various established methods in medical research (block 14). For example, specific genes, such as Yamanaka factors, may be used to reprogram the adult cells into stem cells, such as induced pluripotent stem cells (iPSCs). Alternatively, the isolated adult cells may be transformed into continuous cell lines by telomerase reverse transcriptase overexpression. In other embodiments, other types of cells may be isolated such as adult stem cells and embryonic stem cells. In this regard, it will be understood that the methods of the present disclosure include all sources of cell lines.

At the next block 16, the cells are grown into a solid or semi-solid structure mimicking an animal organ, such as a fish organ, by attaching/adhering to a food-grade biocompatible scaffold or extracellular matrix in a sterile chamber or container, such as a bioreactor. The sterile chamber or container may be temperature controlled, and may have inlets and outlets for introducing and removing substances such as chemicals, nutrients, and cells. In some embodiments, block 16 is carried out in the absence of antibiotics or antimicrobial compounds in the sterile container. Block 18 involves supplying the culture medium to the bioreactor to support cell survival and growth. The culture medium may be a buffered solution containing components such as, but not limited to, inorganic salts (e.g., calcium chloride ($CaCl_2$)), potassium chloride (KCl), sodium chloride (NaCl), sodium bicarbonate ($NaHCO_3$), sodium dihydrogen phosphate ($NaH_2PO_4$), magnesium sulfate ($MgSO_4$), etc.), amino acids, vitamins (e.g., thiamine, riboflavin, folic acid, etc.), and other components such as glucose, β-mercaptoethanol, ethylenediaminetetraacetic acid (EDTA), and sodium pyruvate. Non-limiting examples of growth media include, but are not limited to, Leibovitz's L-15 medium, Eagle's Minimum Essential Media (MEM), Medium 199, Dulbecco's Modified Eagle Medium (DMEM), Ham's F12 Nutrient Mix, Ham's F10 Nutrient Mix, MacCoy's 5A Medium, Glasgow Modified Eagle Medium (GMEM), Iscove's Modified Dulbecco's Medium, and RPMI 1640.

According to block 20, food-grade growth factors and cytokines are introduced into the culture medium in the bioreactor to support cell growth and proliferation. The growth factors and cytokines may include, but are not limited to, insulin growth factor 1 (IGF-1), insulin, interleukin 6 (IL-6), interleukin 6 receptor (IL-6R), interleukin 11 (IL-11), fibroblast growth factor (FGF), epidermal growth factor (EGF), and transferrin. Block 20 may involve co-culturing bioengineered cells with the isolated cells in the absence of fetal bovine serum (FBS). The bioengineered cells are engineered to secrete the above growth factors and cytokines, and supply these biomolecules to the isolated cells as needed for growth and proliferation.

As used herein, "bioengineered" cells are not equivalent to genetically modified cells. The bioengineered cells have a specific gene that overexpresses one or more specific proteins. The bioengineered cells may be fish cells, or other types of animal cells, such as cow cells. The bioengineered cells are not present in the final meat product. As non-limiting examples, bioengineered fish cells may be co-cultured with isolated fish cells, or bioengineered cow cells may be co-cultured with isolated cow cells. The co-culturing method of the present disclosure eliminates the need for animal-derived fetal bovine serum (FBS) in the culture medium. Furthermore, the co-culturing method provides a continuous supply of food-grade specific growth factors and cytokines to the growing isolated cells in situ, and simplifies and reduces the cost of the production process. However, in other embodiments, FBS or other serum may be used to supply growth factors, cytokines, and other nutrients to support cell growth during block 16.

Figure 2:
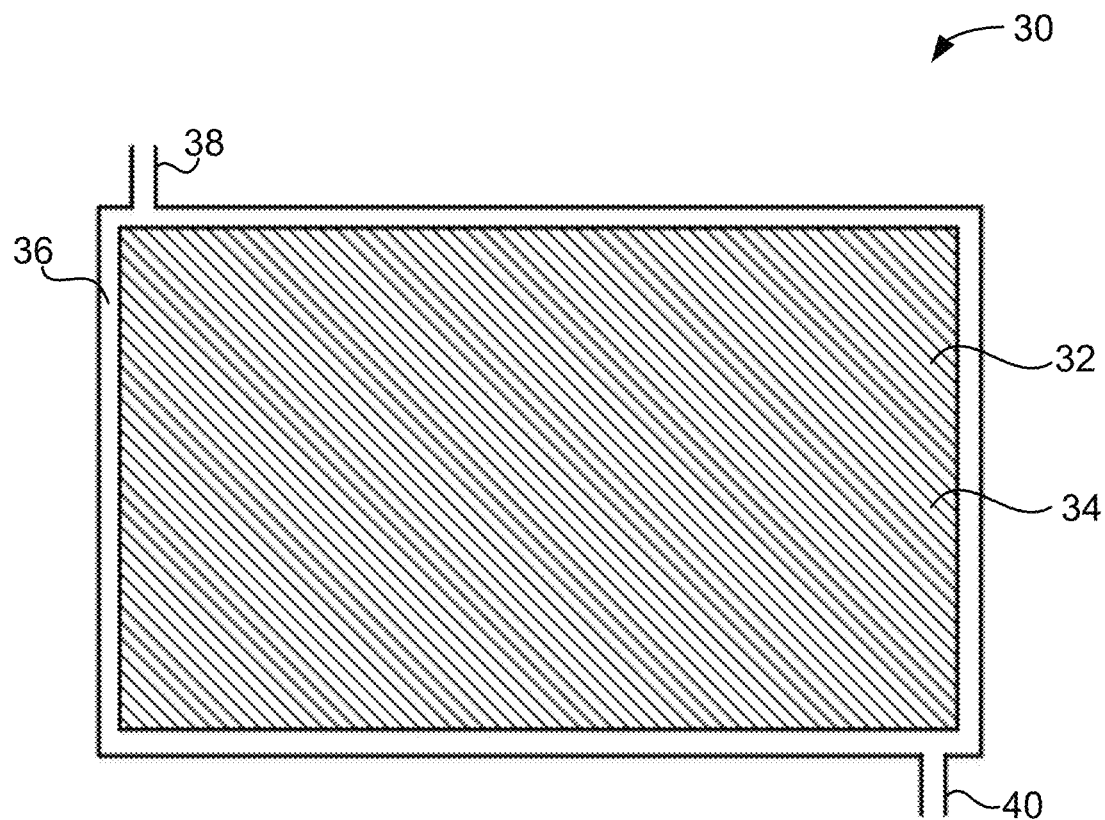
FIG. 2 is a schematic or conceptual cross-sectional view of a bioreactor used for in vitro meat production having solid phase support, according to one embodiment of the present disclosure.

Turning to FIG. 2, an exemplary bioreactor 30 used for culturing the isolated cells and/or in vitro meat production is shown. The cells attach to and grow on solid-phase support 32 provided by a food-grade scaffold or extracellular matrix 34 which is held in a sterile chamber 36 in the bioreactor 30. The scaffold or extracellular matrix 34 may dictate the shape of the meat product. The food-grade scaffold may be made of plant-based or fungi-based materials such as, but not limited to, agarose, alginate, chitosan, mycelium, and konjac glucomannan. The solid phase support 32 may be porous so that the cells may attach to and grow on the inner surfaces of the support 32. The culture medium supplying nutrients to the cells is introduced into the bioreactor 30 through an inlet 38, and is emptied from the bioreactor 30 through an outlet 40.

Figure 3:
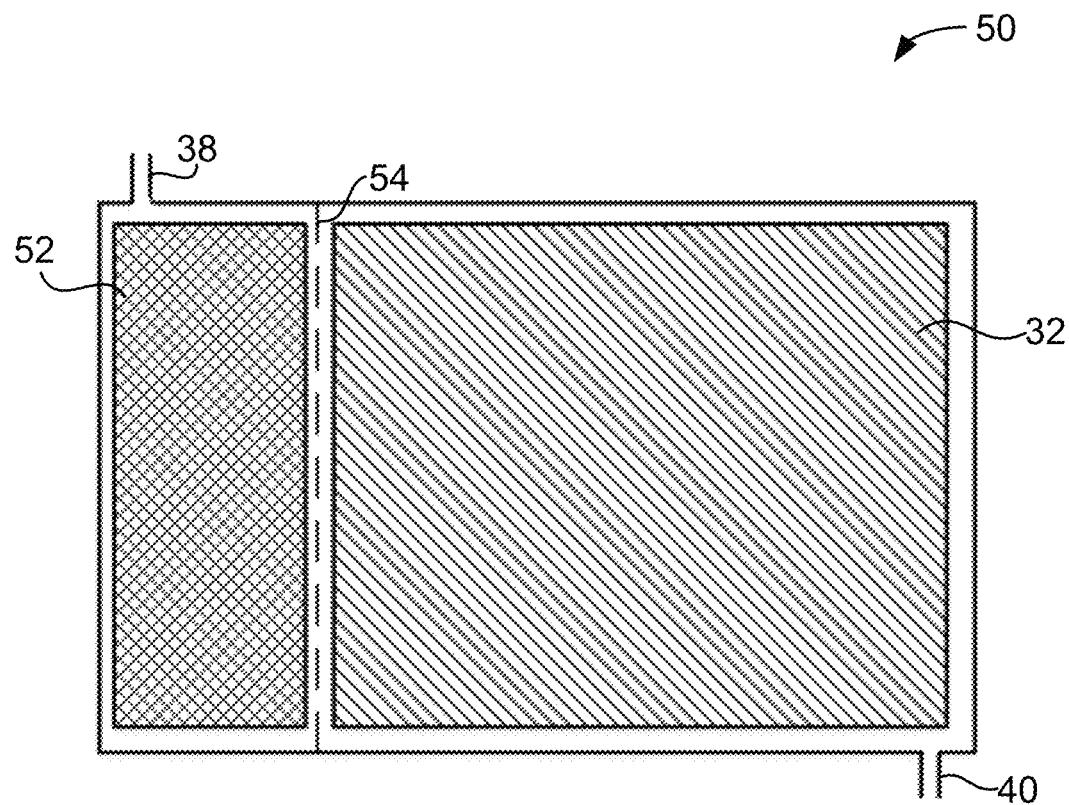
FIG. 3 is a schematic or conceptual cross-sectional view of a bioreactor similar to FIG. 2 but having a second solid phase, according to one embodiment of the present disclosure.

FIG. 3 shows a bioreactor 50 similar to the bioreactor 30 of FIG. 2, but further includes a second solid phase 52 separated from the solid phase support 32 by a fine mesh 54. The second solid phase 52 may contain or support the bioengineered cells that secrete nutrients, growth factors, and cytokines for the cells growing on the solid phase support 32 in situ, and may physically separate the bioengineered cells from the cells on the solid phase support 32. The second solid phase 52 is made of plant-based materials, similar to the solid phase support 32. The mesh 54 is permeable to nutrients, growth factors, and cytokines, but is impermeable to cells. The bioreactor 50 of FIG. 3 allows the co-culturing of the bioengineered cells with the growing cells. In some embodiments, the bioreactors 30 and 50 of FIGS. 2 and 3 may be arranged in tandem. In other embodiments, several of the bioreactors 30, several of the bioreactors 50, or mixtures of the bioreactors 30 and 50 may be arranged in series for scaling up the process. The bioreactor 30 may be used mainly for biomass production, whereas the bioreactor 50 may be used for providing nutrients, growth factors, and cytokines to the growing cells.

Figure 4:
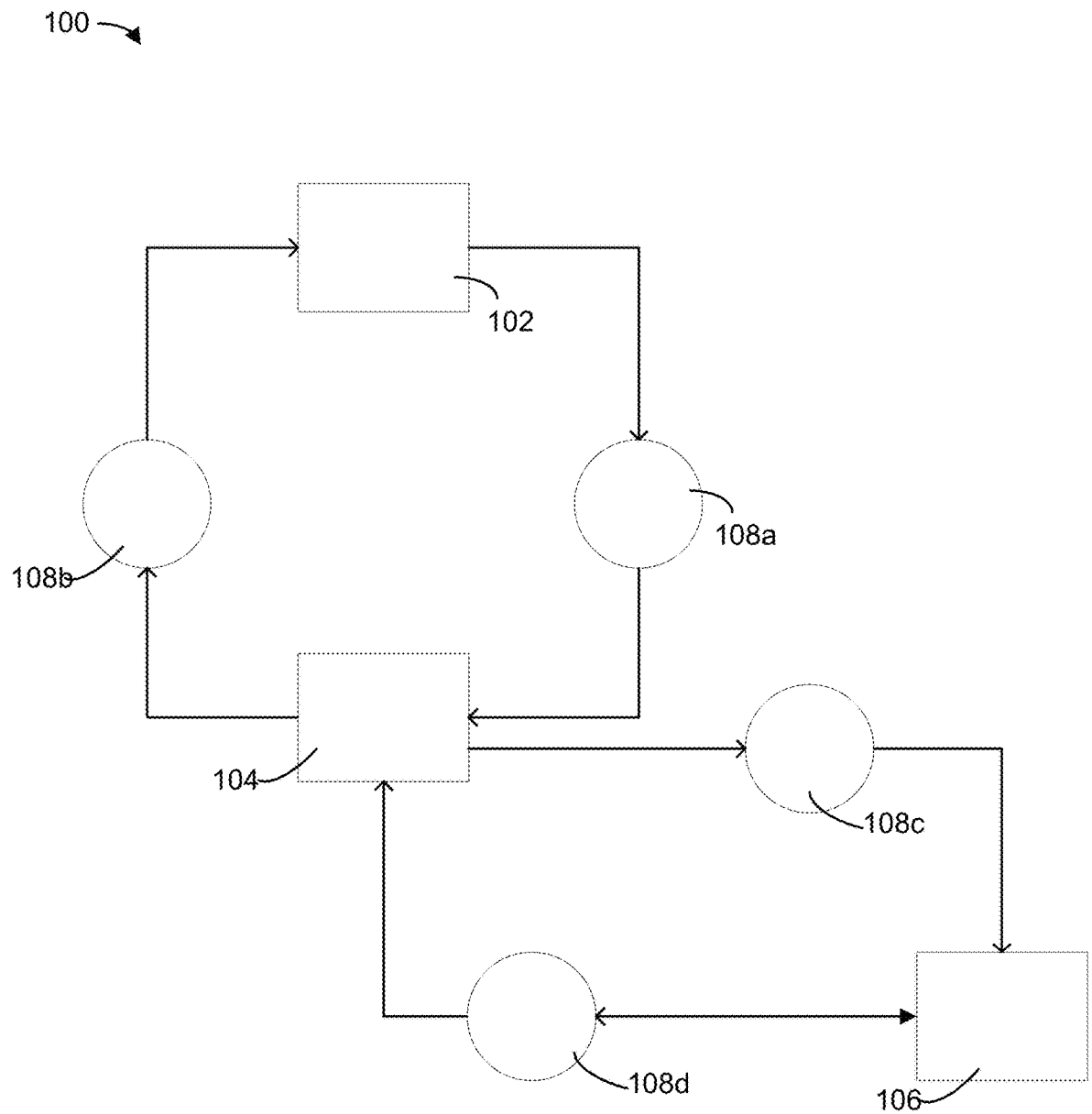
FIG. 4 is a schematic view of a cell culture system according to one embodiment of the present disclosure.

Turning to FIG. 4, an exemplary cell/tissue culture system 100 comprises a cell culture unit 102, a fresh medium unit 104 and a waste removal unit 106. The cell culture unit 102 is connected to the fresh medium unit 104 through pumps 108a and 108b such that a first fluid may flow from bioreactor 102 to the fresh medium unit 104 through pump 108a and the first fluid may flow from the fresh medium unit 104 to the bioreactor 102 through pump 108b. Thereby the first fluid circulates between the bioreactor 102 and the fresh medium unit 104. The tube for the circulation of the first fluid and at least one of the pumps 108a and 108b are configured to create a fluid flow that evenly distributes nutrients inside the bioreactor 102. Such fluid flow is achieved in the absence of a stirrer or agitator in the cell/tissue culture system 100.

The fresh medium unit 104 is further connected to the waste removal unit 106 through pumps 108c and 108d such that a second fluid may flow from the fresh medium unit 104 to the waste removal unit 106 through pump 108c and the second fluid may flow from the waste removal unit 106 to the fresh medium unit 104 through pump 108d. Thereby, the second fluid circulates between the fresh medium unit 104 and the waste removal unit 106. The first fluid may be a cell culture medium which may include a basal medium supplemented with FBS, growth factors or cytokines. Growth factors or cytokines may include but are not limited to, insulin growth factor 1 (IGF-1), insulin, interleukin 6 (IL-6), interleukin 6 receptor (IL-6R), interleukin 11 (IL-11), fibroblast growth factor (FGF), epidermal growth factor (EGF), and transferrin. The second fluid may be a fresh basal medium (dialysate) which may include a buffered solution containing components such as, but not limited to, inorganic salts (e.g., calcium chloride (CaCl2)), potassium chloride (KCl), sodium chloride (NaCl), sodium bicarbonate (NaHCO3), sodium dihydrogen phosphate (NaH2PO4), magnesium sulfate (MgSO4), etc.), amino acids, vitamins (e.g., thiamine, riboflavin, folic acid, etc.), and other components such as glucose, beta-mercaptoethanol, ethylenediaminetetraacetic acid (EDTA), and sodium pyruvate. Non-limiting examples of growth media include, but are not limited to, Leibovitz's L-15 medium, Eagle's Minimum Essential Media (MEM), Medium 199, Dulbecco's Modified Eagle Medium (DMEM), Ham's F12 Nutrient Mix, Ham's F10 Nutrient Mix, MacCoy's 5A Medium, Glasgow Modified Eagle Medium (GMEM), Iscove's Modified Dulbecco's Medium, and RPMI 1640.

The pumps 108 may be peristaltic pumps or any other similar suitable pumps.

The cell/tissue culture system 100 includes one or more vessels. Each bioreactor 102, fresh medium unit 104 and waste removal unit 106 may be a vessel. In some embodiments, the cell/tissue culture system 100 may include more than one bioreactor 102, fresh medium unit 104 and waste removal unit 106. The plurality of bioreactor 102 may be connected in parallel or series and disposed in proximity to each other. The plurality of fresh medium unit 104 may be connected in parallel or series and disposed in proximity to each other. The plurality of waste removal unit 106 may be connected in parallel or series and disposed in proximity to each other. In some embodiments, the cell/tissue culture system 100 may include more than one bioreactor 102 connected in parallel with a single fresh medium unit 104 and the waste removal unit 106. In some embodiments, the size or the volume of the bioreactor 102 may vary. As such, the production of the cell/tissue culture system 100 can be scaled up and down easily.

In some embodiments, the cell/tissue culture system 100 may further include a gas source configured to supply gas to the cells in the bioreactor 102. The gas source may be nitrogen. oxygen, carbon dioxide or a mixture of gases.

The bioreactor 102 is configured to hold scaffold or extracellular matrix and culture medium such that cells may grow into tissue in a solid or semi-solid structure. In some embodiments, the cells are grown into a solid or semi-solid structure mimicking an animal organ, such as a fish organ, by attaching/adhering to a food-grade biocompatible scaffold or extracellular matrix to the interior of the bioreactor 102. The bioreactor 102 may be configured to contain at least one type of cell. Suitable types of cells include, but not are not limited to, bone, cartilage, muscle, liver, skin, heart, lung and any combinations thereof. Other types of mammalian cells or fish cells may be used within the present invention. Cells from other plant and animal species can be used. Other starter cells may be stem cells of various origins such as mesenchymal stem cells, induced pluripotent stem cells and satellite cells. The starter cells may also be genetically modified cells or any cell lines. Bioengineered cells may be used as well.

Different types of specialized cells to be expanded in the bioreactor 102 may be obtained by biopsy from live animals.

The bioreactor 102 may further include an inlet configured to receive the first fluid from the fresh medium unit 104 through pump 108b and an outlet configured to remove/release the first fluid to the fresh medium unit 104 through pump 108a. Bioreactor 102 may further include a heating device configured to heat the interior of the bioreactor 102 to a predetermined temperature and a temperature control unit to maintain the temperature within the bioreactor 102 at such a predetermined temperature. The predetermined temperature can be approximately ranged from 25° C. to 45° C.

The bioreactor 102 may further include at least one stirrer configured to stir the first fluid within the bioreactor 102 at a predetermined speed. The predetermined can be approximately from 10 rotations per minute (rpm) to 300 rpm. In some embodiments, the pump and the tube connected to the bioreactor 102 are configured to create a fluid flow that evenly distributes nutrients inside the bioreactor 102. Such fluid flow is achieved in the absence of a stirrer or agitator in the cell/tissue culture system 200.

The bioreactor 102 may further include a gas outlet and a gas inlet connected to the gas source, which may be nitrogen, oxygen, carbon dioxide or a mixture of gases. Gases may be fed into the bioreactor 102 through the gas inlet to optimize cell culture conditions. Wasted gas may be released through the gas outlet. The flow of the gas may be controlled by a valve.

In some embodiments, the bioreactor 102 could be the bioreactor 30 as shown in FIG. 2. Yet in some embodiments, the bioreactor 102 could be the bioreactor 50 as shown in FIG. 3. In some embodiments, the bioreactor 102 is a vessel. In some embodiments, the bioreactor 102 may be any size. In some embodiments, the volume of the bioreactor 102 may be ranged from 0.1 L-2000 L.

Figure 5:
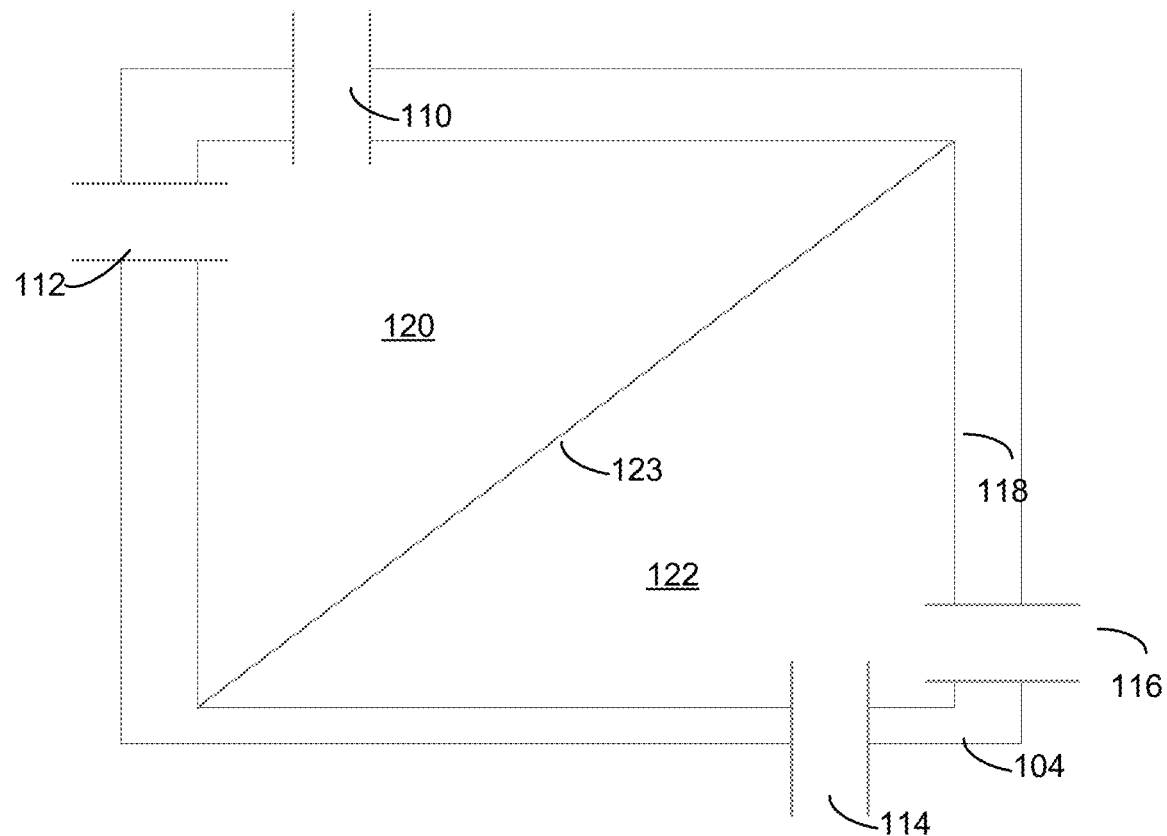
FIG. 5 is a schematic view of a fresh medium unit according to one embodiment of the present disclosure.

Turning to FIG. 5, the fresh medium unit 104 may comprise a first fluid medium inlet 110 and a first fluid outlet 112 configured to connect to pump 108a and pump 108b respectively. In addition, the fresh medium unit 104 may further comprise a second fluid inlet 114 and a second fluid outlet 116 configured to connect to pump 108d and pump 108c respectively. In addition, the fresh medium unit 104 may comprise at least one first dialysis unit 118 having a first fluid compartment 120 and a second fluid compartment 122 separated by a first dialysis membrane 123. The first fluid inlet 110 and the first fluid outlet 112 are connected to the first fluid compartment 120. The second fluid inlet 114 and the second fluid outlet 116 are connected to the second fluid compartment 122. Different types of dialysis membrane 123 including Cellulose Ester (CE), Regenerated Cellulose (RC) or Polyvinylidene fluoride (PVDF) may be used. Dialysis membrane 123 of different molecular weight cut-off (MWCO) may be used to retain desirable macromolecules in the first fluid (e.g. growth factors secreted by cells in culture vessel) and allow waste to be removed from the first fluid in the first dialysis unit 118. The desirable macromolecules may also include different kinds of proteins and other macromolecules in the first fluid (both having at least 100 Da), for example, phospholipid (lecithin, ceramide), lipid (DHA, AHA), polysaccharide (glycogen), proteoglycan (heparin, chondroitin), nucleic acid (DNA, RNA), insulin-like growth factor (IGF, 7.5 kDa for a recombinant form) and transforming growth factor-beta (TGF beta, 44 kDa for pro TGF-beta). For example, 100 Da-1,000,000 Da MWCO membrane, preferably 500 Da MWCO membrane, can be used to retain insulin-like growth factor (IGF, 7.5 kDa for a recombinant form) and transforming growth factor-beta (TGF beta, 44 kDa for pro TGF-beta) in the first fluid and allow lactate (89 Da) and ammonia (17 Da) to be removed from the first fluid. Such membrane may also be used to allow nutrients of the second fluid such as glucose (180 Da) to get across the membrane into the first fluid for replenishment. In some embodiments, the dialysis unit 118 may be in a form of a hollow fiber cartridge containing semipermeable hollow fibers.

The fresh medium unit 104 may comprise at least one stirrer in either or both compartments configured to stir the fluid within the dialysis unit at a predetermined speed. The predetermined speed can be approximately from 10 rpm to 500 rpm.

The fresh medium unit 104 may further include a separated inlet and outlet connected to either or both compartments to add, replenish and remove desired fluid. The desired fluid may be cell culture medium, fresh basal medium and/or differentiation medium (all of which contain the nutrients for the cells in the bioreactor 102).

Figure 6:
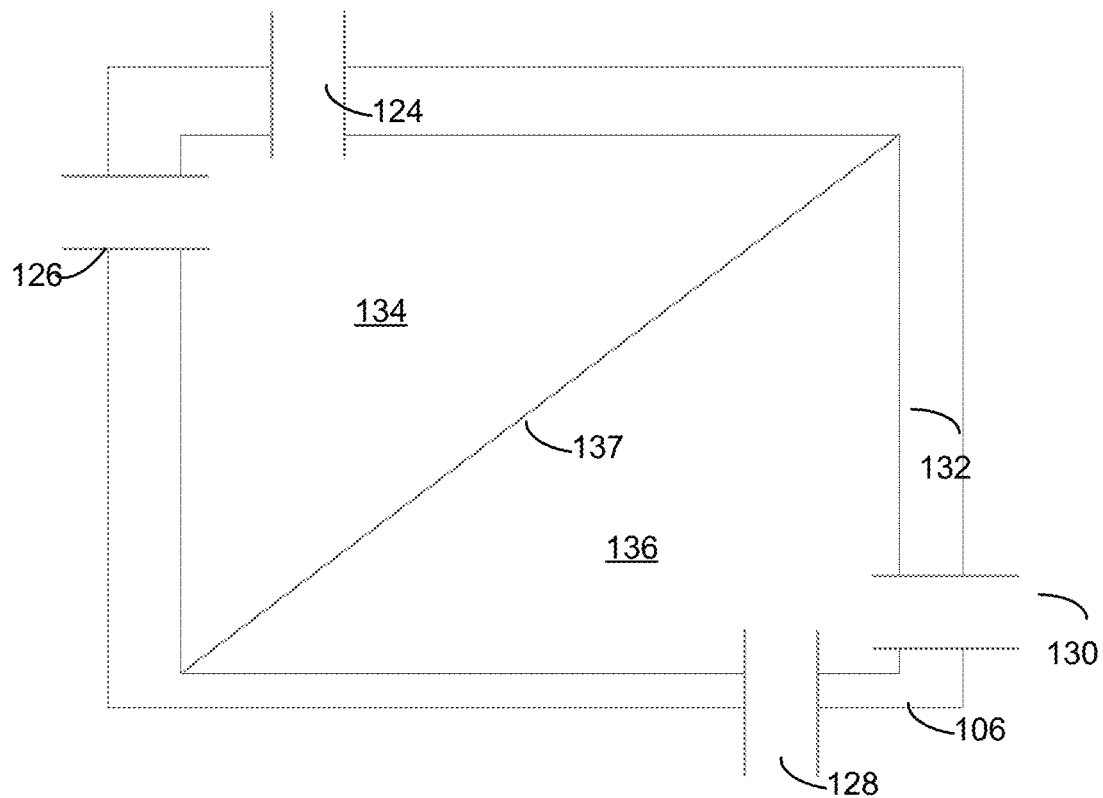
FIG. 6 is a schematic view of a waste removal unit according to one embodiment of the present invention.

Turning to FIG. 6, the waste removal unit 106 may comprise a waste inlet 124 and a refresh outlet 126 configured to connect to pump 108c and pump 108d respectively. In addition, the waste removal unit 106 may further comprise a waste removal inlet 128 and a waste removal outlet 130. In addition, the waste removal unit 106 may comprise at least one second dialysis unit 132 having a waste compartment 134 and a waste removal compartment 136 separated by a second dialysis membrane 137. The waste inlet 124 and the fresh medium outlet 116 are connected to the waste compartment 134. The waste removal inlet 128 and the waste outlet 130 are connected to the waste removal compartment 136. In some embodiments, the dialysis unit 132 may be in a form of a hollow fiber cartridge containing semipermeable hollow fibers. The waste removal unit 106 may use other waste removal techniques to remove wastes from the second fluid. For example, waste removal may be carried out by passing the second fluid through zeolite as adsorbents. Zeolites are microporous, aluminosilicate minerals. Examples are analcime, chabazite, clinoptilolite, heulandite, natrolite, phillipsite, and stilbite. The waste removal unit 106 may include a column of packed-bed zeolite. The second fluid flows into the waste removal unit 106 from one end, passing through the zeolite and exiting the waste removal unit 106 from another end. The zeolite absorbs toxic chemicals or chemicals inhibiting cell growth in the second fluid, e.g. ammonia and lactate.

The waste removal unit 106 is configured to remove metabolic wastes such as ammonia and lactate in a second fluid and allow retention of the maximum amount of nutrients such as glucose in the waste medium. A dialysis membrane of 100 Da-1,000,000 Da MWCO, preferably 100 Da MWCO, may be used to allow ammonia and lactate to get into the dialysate with glucose retained in the second fluid. Dialysate, which enters the waste removal compartment 136 can be phosphate-buffered saline (PBS) or any other possible buffers.

In some embodiments, each of the bioreactor 102, fresh medium unit 104 and waste removal unit 106 may be a removable plug-in module. In other words, each of the bioreactor 102, fresh medium unit 104 and waste removal unit 106 is detachably connected to the cell/tissue culture system 100. Each of the inlets and outlets of the foregoing units may connect and/or disconnect with the inlets and outlets of the pumps of the cell/tissue culture system 100. For example, a fresh medium unit 104 or the waste removal unit 106 may be quickly replaced by unplugging it from the system and plugging a new unit into the cell/tissue culture system 100. The present embodiment could reduce the downtime if one of the units is malfunctioned. Furthermore, each of the units can be unplugged from the cell/tissue culture system 100 and operates on its own for independent use.

Now, turning to the method of utilizing the cell/tissue culture system 100 to grow cell culture and tissues. The method describes herein may be used to culture cells and tissues such as skin, muscle, adipose and bone cells to produce cultured meat. The method includes providing the cell/tissue culture system 100 having a bioreactor 102, transferring of cultured medium with metabolic wastes or growth inhibitors into the first dialysis unit 118 of the fresh medium unit 104, replenishing nutrient to the cultured medium and removing growth inhibitors from the cultured medium in the first dialysis unit 118 of the fresh medium unit 104, transferring of basal medium with metabolic waste or growth inhibitors from the first dialysis unit 118 of the fresh medium unit 104 to the waste removal unit 106, and removing growth inhibitors and metabolic waste from the basal medium in the waste removal unit 106. As such, the metabolic waste and growth inhibitors in the bioreactor 102 are removed and the nutrients are replenished to the cells in the bioreactor 102 through first dialysis unit 118.

At least one type of cell is added to the bioreactor 102. Suitable types of cells include, but are not limited to, bone, cartilage, muscle, liver, skin, heart, lung and any combinations thereof. Other types of mammalian cells or fish cells may be used within the present invention. Cells from other plant and animal species can be used.

Different types of specialized cells to be expanded in the culture vessel may be obtained by biopsy from live animals. Other starter cells may be stem cells of various origins such as mesenchymal stem cells, induced pluripotent stem cells and satellite cells. The starter cells may also be genetically modified cells or any cell lines.

The cells are grown into tissue in a solid or semi-solid structure mimicking an animal organ, such as a fish organ, by attaching/adhering to a food-grade biocompatible scaffold or extracellular matrix in a sterile chamber or container, such as the bioreactor 102. In some embodiments, the bioreactor 102 comprises a tissue culture holder, which may be configured to hold the food-grade scaffold or a layer of the extracellular matrix that accommodates cell growth thereon. The growing cells may be instructed to deposit extracellular matrix under predetermined conditions. The scaffold or extracellular matrix provides a three-dimensional structure for the cells to develop and form tissue. The cell culture holder may have a plurality of scaffold or extracellular matrix holders, each holder may be configured to receive and hold at least one scaffold or extracellular matrix. It may also receive and hold a plurality of scaffolds or extracellular matrices at different thicknesses, which may be stacked in the holder. The tissue culture holder may further comprise a fluid permeable structure to allow fluid in the bioreactor 102 to interact with cells on the scaffold or extracellular matrix from all sides. The tissue culture holder may be made of a material that would not be damaged by regular sterilizing methods known in the art, for example, disinfectant agent, ultraviolet light and autoclave. Such material, for example, may be stainless steel, glass or high temperature resistance resin. More than one tissue culture holder may be held in a sterile chamber of the bioreactor 102, thus allowing easy scale-up according to production demands. For some embodiments, the tissue culture holder may be a supporting tray or porous plate, wherein such tray or plate includes at least one porous which allows medium flow.

The tissue culture holder is configured to optimize the exchange of nutrients and waste between the cells and the culture medium while minimizing the flow of the culture medium at the tissue culture holder to reduce the shear stress acting on the cells because the developing tissue is not directly perfused and nutrients are delivered by diffusion. Excessive shear stress could kill cells which leads to low yield. The tissue culture holder may further include a holder to hold a scaffold or an extracellular matrix to fix its position in the tissue culture holder. The tissue culture holder is optimized such that its vibration is minimized as the culture medium flows. It helps the cells to attach to the scaffold or the extracellular matrix firmly, thus enhancing the yield.

In yet some embodiments, the bioreactor 102 does not include culture holder, food-grade scaffold and extracellular matrix. The cells in the bioreactor 102 may be cultured in suspension in the bioreactor 102. The bioreactor 102 may further configured to control the shear stress in the bioreactor 102 in order to lower the shear stress acting on the cells. Yet, the bioreactor 102 may include microcarriers such that the cell may proliferate on it.

The temperature of the bioreactor 102 is controlled and the culture medium is introduced into the bioreactor 102 at its inlet and released from the bioreactor 102 outlet to remove substances such as chemicals, nutrients, growth inhibitors and cells. The food-grade biocompatible scaffold becomes part of the final edible product.

Growth factors, plant hydrolysates, plant extracts and cytokines from fetal bovine serum (FBS) supplements or recombinant sources are introduced into the culture medium in the bioreactor to support cell growth and proliferation. The growth factors and cytokines may include, but are not limited to, insulin growth factor 1 (IGF-1), insulin, interleukin 6 (IL-6), interleukin 6 receptor (IL-6R), interleukin 11 (IL-11), fibroblast growth factor (FGF), epidermal growth factor (EGF), and transferrin. The application may involve co-culturing bioengineered cells with the cultured cells in the bioreactor 102 in the absence of FBS. The bioengineered cells are engineered to secrete the above growth factors and cytokines and supply these biomolecules to the cultured cells as needed for growth and proliferation. The co-culturing method of the present disclosure eliminates the need for animal-derived fetal bovine serum (FBS) in the culture medium. Furthermore, the co-culturing method provides a continuous supply of food-grade specific growth factors and cytokines to the growing isolated cells in situ and simplifies and reduces the cost of the production process. However, in other embodiments, FBS, other serum or proteins from recombinant sources may be used to supply growth factors, cytokines, and other nutrients to support cell growth.

In some embodiments, gases may be introduced to optimize cell culture conditions. Nitrogen, oxygen, carbon dioxide or a mixture of gases may be used. The bioreactor 102 may contain 0-10% of carbon dioxide. The bioreactor 102 may contain 15-30% of oxygen. The bioreactor 102 may contain 60-85% of nitrogen.

In some embodiments, the temperature may be controlled to optimize the cell culture conditions. Different types of cells may have different optimal culture temperatures. The temperature may be ranged from 25-45° C.

In some embodiments, the culture medium in the bioreactor 102 is stirred. The stirring speed in the culture vessel may be optimized to enhance the expansion of cells as it is known that cells react differently to shear stress. Stirring speed may also be optimized to enhance the mixing of inflow culture medium and culture medium inside the bioreactor 102. Stirring speed may be ranged from 10 rpm-300 rpm.

The pump 108a may transfer the culture medium from the bioreactor 102 to the first dialysis unit 118 of the fresh medium unit 104.

In the first dialysis unit 118, different types of dialysis membrane including CE, RC or PVDF may be used. Dialysis membrane of different molecular weight cut-off (MWCO) may be used to retain desirable macromolecules in culture medium (i.e. the first fluid in this particular embodiment) (e.g. growth factors secreted by cells in culture vessel) and allow waste to be removed from the culture medium in the first dialysis unit 118. For example, 100 Da-1,000,000 Da MWCO membrane, preferably 500 Da MWCO membrane, can be used to retain insulin-like growth factor (IGF, 7.5 kDa for a recombinant form) and transforming growth factor-beta (TGF beta, 44 kDa for pro TGF-beta) in the culture medium and allow lactate (89 Da) and ammonia (17 Da) to be removed from the culture medium. Such membrane may also be used to allow nutrients of fresh basal medium/dialysate (i.e. second fluid in this particular embodiment) such as glucose (180 Da) to get across the membrane into the culture medium for replenishment.

The fresh basal medium fills the second fluid compartment 122 while the culture medium fills the first fluid compartment 120 to perform dialysis. For example, lactate, ammonia and other wastes are transferred from the culture medium to the fresh basal medium through the first dialysis membrane 123 and the glucose and other growth-enhancing compounds are transferred from the fresh basal medium to the culture medium through the first dialysis membrane 123. The rate of dialysis can be controlled by changing the volume of the fresh basal medium, the volume of the culture medium contained within the dialysis membrane, membrane surface area, temperature, and agitation by stirring in the dialysis unit. The rate of nutrient replenishment and waste removal of culture medium in the dialysis unit may also be controlled by changing pumping speed ranged from 1 ml/min-10 L/min for fluid inflow from the bioreactor 102 into the first fluid compartment 120 of the first dialysis unit 118.

Metabolic wastes or growth inhibitors move from the culture medium into the fresh basal medium inside the first dialysis unit 118. Growth inhibitors accumulate in the fresh basal medium over time. Basal medium with accumulated growth inhibitors (including but not limited to lactate, ammonia) is referred to as waste medium herein. The waste medium may be transferred to a waste removal unit 106 by pump 108c. Metabolic wastes such as ammonia and lactate in the waste medium may be removed by using the dialysis principle at the second dialysis unit 132 of the waste removal unit 106. Waste removal methods should allow the retention of the maximum amount of nutrients such as glucose in the waste medium. A dialysis membrane of 100 Da-1,000,000 Da WMCO membrane, preferably 100 Da MWCO membrane, may be used to allow ammonia and lactate to get into the dialysate with glucose retained in the waste medium. The dialysate can be phosphate-buffered saline (PBS) or any other possible buffers. The rate of dialysis can be controlled by changing the volume of the dialysate, the volume of the waste medium contained within dialysis membrane 137, membrane surface area, temperature, and agitation by stirring in the dialysis unit 132. Stirring speed may be ranged from 10 rpm-500 rpm. The rate of waste removal in waste removal unit 106 may also be controlled by changing pumping speed for fluid inflow from the first dialysis unit 118 of the fresh medium unit 104 into the waste removal unit 106. Waste medium cleaned by dialysis can be transferred back to the first dialysis unit 118 of the fresh medium unit 104. The pumping speed may be ranged from 1 ml/min-10 L/min.

The separation of the cell/tissue culture from the fresh basal medium unit 104 and waste medium unit 106 allows the bioreactor 102 to be kept closed securely throughout production. Contaminations in any of the units will be confined to the affected unit and will not affect other units.

Furthermore, waste removal unit 106 helps to centralize, extracting and/or collecting the metabolic wastes from the whole cell/tissue culture system 100 by extracting such wastes from the second fluid. The wastes of the whole cell/tissue culture system 100 can then be easily collected and discharged. It reduces the wastes discharged and the overall running cost of cell culturing compared to the conventional cell culturing technique. As discussed in the background section, the conventional cell culturing technique discards spent culture medium containing both nutrients and wastes and replaces it with a new culture medium. Therefore, the amount/volume of waste (i.e. the spent culture medium) created in the conventional method is more than the amount/volume of waste created in the present invention.

Yet, the fresh medium unit 104 and waste removal unit 106 help lower the running cost and optimize medium use for growing cell cultures. The cell culture medium is generally more expensive than basal medium as the cell culture medium contains expensive FBS, growth factors or cytokines. With the help of the fresh medium unit 104, the cell culture medium does not need to be prematurely discarded and can be refreshed (i.e. removing waste thereof and obtaining nutrients from the basal medium).

Different types of cells include but are not limited to skin, bone, cartilage, heart, and liver can be cultured in suitable scaffolds or extracellular matrix to form tissues in the bioreactor 102. Stem cells of various origins such as mesenchymal stem cells, induced pluripotent stem cells and satellite cells can also be cultured in suitable scaffolds for tissue engineering applications. Components of differentiation medium can be added into the basal medium in the first dialysis unit 118 or second dialysis unit 132 for subsequent differentiation after an expansion of stem cells in scaffolds or extracellular matrix to form functional engineered tissues. For example, osteoinduction medium components such as dexamethasone, ascorbic acid and β-Glycerophosphate can be added to the basal medium for osteogenic differentiation of stem cells in scaffolds. The first dialysis membrane 123 of may be ranged from 100 Da-1,000,000 Da MWCO, preferably 500 Da MWCO, should be selected to allow the components of the osteoinduction medium to get into the culture medium.

Alternatively, stem cells can be expanded on a 2D culture surface or on microcarriers in bioreactor 102. Stem cells can be expanded and trypsinized to obtain high-density cell suspensions for regenerative medicine applications. For example, human mesenchymal stem cells can be isolated from patients and expanded on a culture dish or on microcarriers in bioreactor 102. Upon confluence, cells are trypsinized to form a high-density cell suspension. The cell suspension is then injected into the injury sites of patients for healing.

Example 1

Figure 7A:
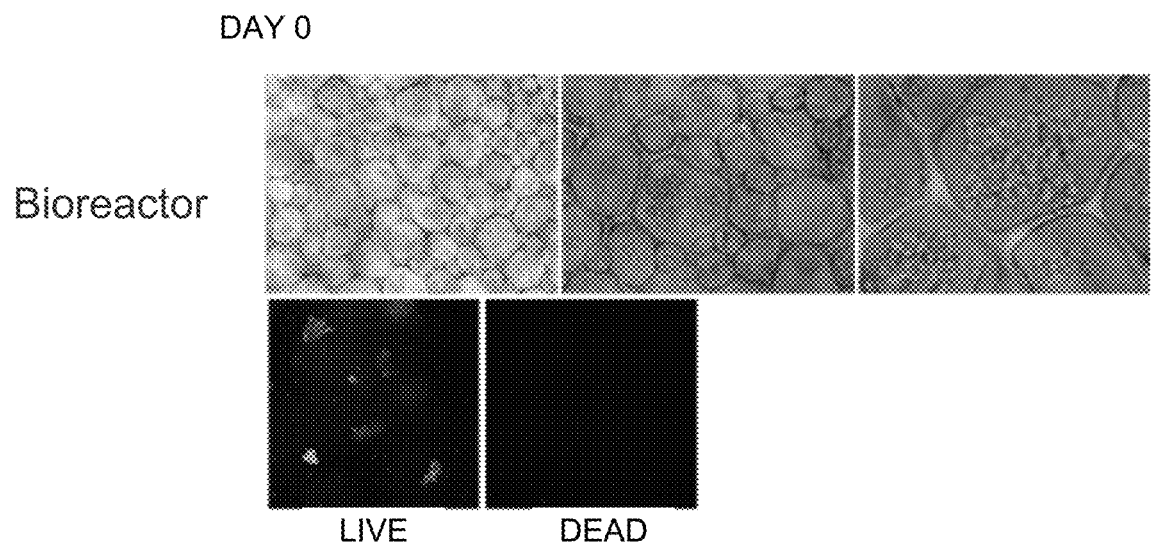
FIG. 7A shows Brightfield images and LIVE/DEAD staining images of HEK293 cells cultured in a collagen-based scaffold on day 0.
Figure 7B:
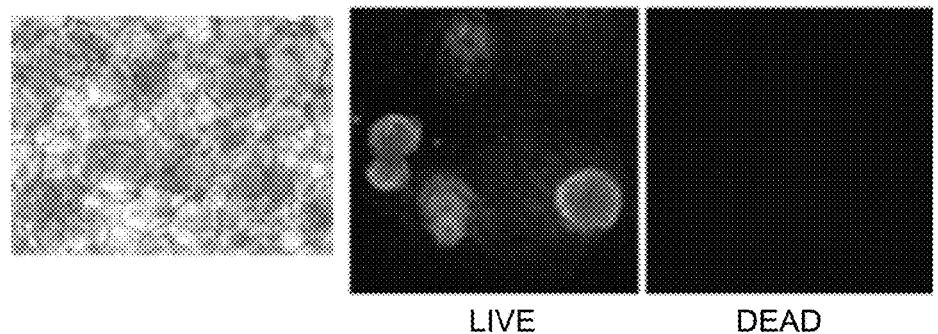
FIG. 7B shows Brightfield images and LIVE/DEAD staining images of HEK293 cells cultured in a collagen-based scaffold on day 4.
Figure 7C:
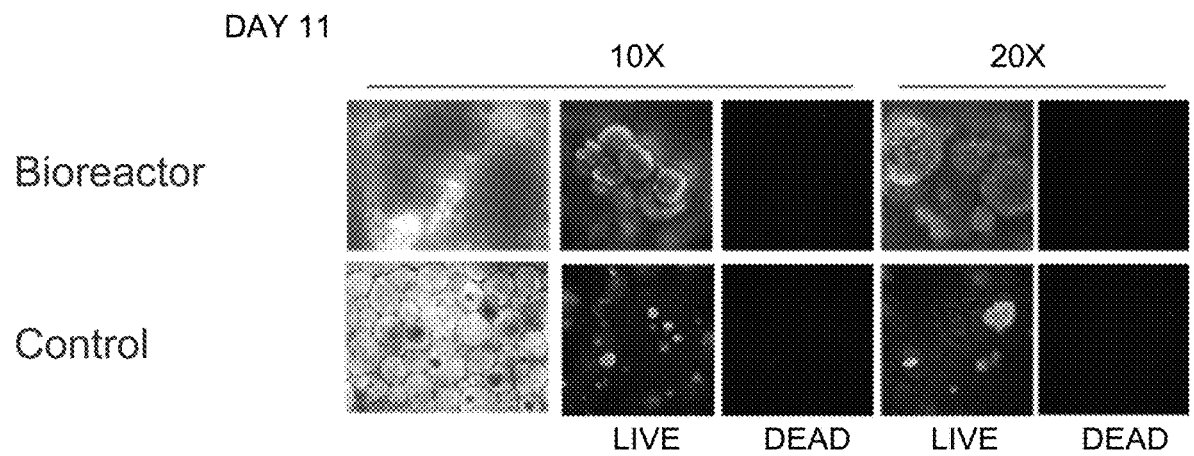
FIG. 7C shows Brightfield images and LIVE/DEAD staining images of HEK293 cells cultured in a collagen-based scaffold on day 11.

A culture of HEK293 cells was washed in PBS and trypsinized to form a cell suspension with a cell density of 2.5e6 cell/ml. A 200 µl cell suspension from 2.5e6 cell/ml suspension was loaded onto a pre-cut square collagen-based scaffold (1 cm×1 cm) to make a tissue construct with a total cell number of 5e5 cells. Tissue constructs were incubated for 4 hours at 37° C. and 5% $CO_2$. 800 µl medium was added along the side of each well gently. Tissue constructs were then transferred into the bioreactor of cell culture unit 102 and a 6-well culture plate for control. On days 0, 4 and 11, images of cells inside scaffolds were captured by a brightfield microscope. On days 0, 4 and 11, LIVE/DEAD staining was performed according to the following protocol. On days 0, 4 and 11, media from the tissue culture bottle, control and the dialysis unit were collected for measurement of glucose.
LIVE/DEAD Staining of Cells in Scaffolds
1. Calcein AM and Ethidium homodimer-1 (LIVE/DEAD kit from Thermo fisher) were added to DPBS at 1:1000 to obtain the staining reagent.
2. Samples were washed in DPBS once.
3. Samples were stained in 200-250 µl staining reagent for 30 minutes.
4. Samples were washed in DPBS once and viewed under a fluorescent microscope.
Results
Observable Microtissues were Formed in the Bioreactor but not in the Control FIGS. 7A-C shows the growth of tissue constructs and cell viability in the bioreactor prototype and control. Bioreactor rows show cells cultured in the working cell culture system prototype. The control row shows cells cultured in a 6-well plate. On day 0, cells attached to the scaffolds as cell aggregates as shown in FIG. 7A. On day 4, cell aggregates grew to larger spheroids in the bioreactor as shown in FIG. 7B. On day 11, spheroids clumped together to form microtissues in the bioreactor while spheroids in control seemed to have no obvious growth as shown in FIG. 7C. LIVE/DEAD staining showed that microtissues in the bioreactor are formed by connecting viable spheroids and they were much larger than those in control.

Figure 8:
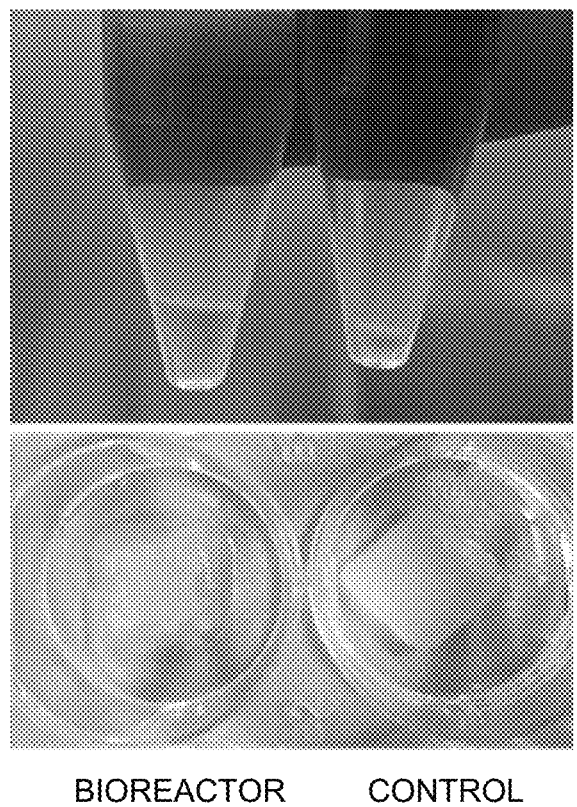
FIG. 8 shows images of extracted cell mass-produced after 11 days of culture in the cell culture system of FIG. 4, the cell mass was extracted from the collagen-based scaffold by trypsinization and centrifugation. Cells that grew in the cell culture system were grown to form microtissues of a much higher volume than those in control. Clumps of microtissues were observed in the cell culture system but not in control. Legend: Bioreactor, cells cultured in the working cell culture system prototype. Control, cells cultured in a 6-well plate.

FIG. 8 shows the microtissues formed on day 11. In the bioreactor, clumps of observable microtissues were formed in the scaffolds and these microtissues were not observed in control. After trypsinization to digest the scaffolds, microtissues were released and, remarkably, microtissues in the bioreactor had a much higher volume than those in control.

Figure 9:
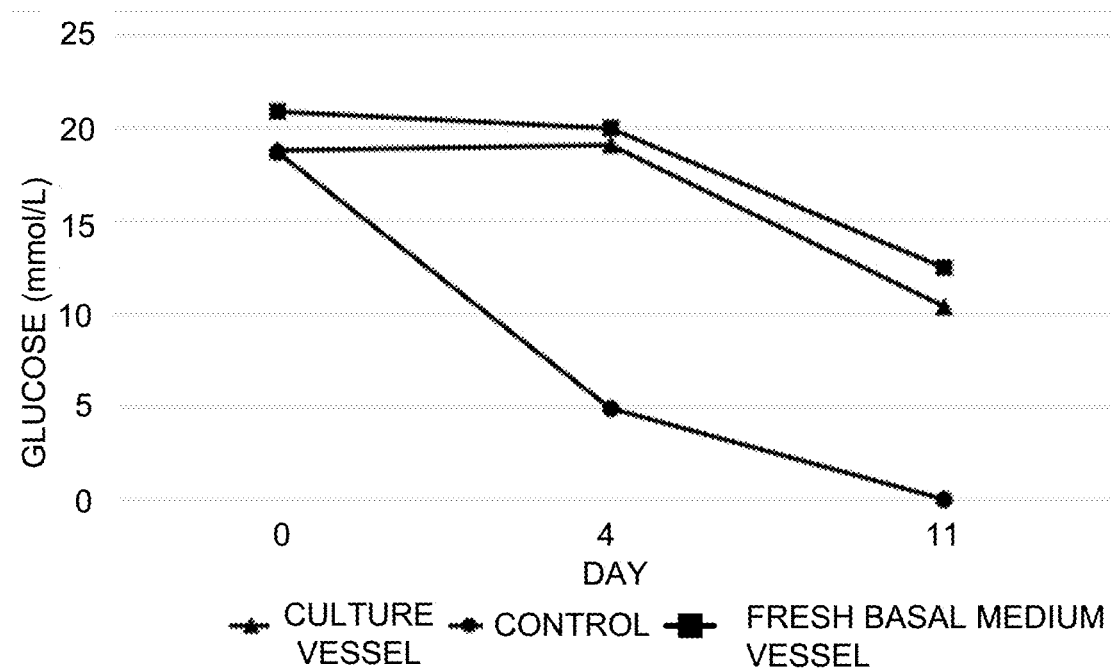
FIG. 9 is a graph of the change in glucose concentration in the culture medium over 11 days of cell culture in the cell culture system and a 6-well plate.

FIG. 9 shows the glucose level was maintained in the culture vessel of the cell culture unit 102 of the bioreactor.

On day 0, Glucose concentration in the culture vessel cell culture unit 102 of the present invention=18.8 mmol/L. Glucose concentration in the control culture plate=18.7 mmol/L. Glucose concentration in the first dialysis unit 118=20.9 mmol/L On day 4, Glucose concentration in the culture vessel cell culture unit 102 of the present invention=19.1 mmol/L. Glucose concentration in the control culture plate=4.9 mmol/L. Glucose concentration in the first dialysis unit 118=20.0 mmol/L.

On day 11, Glucose concentration in the culture vessel cell culture unit 102 of the present invention=10.4 mmol/L. Glucose concentration in the control culture plate=not detectable. Glucose concentration in the first dialysis unit 118=12.5 mmol/L.

Figure 10:
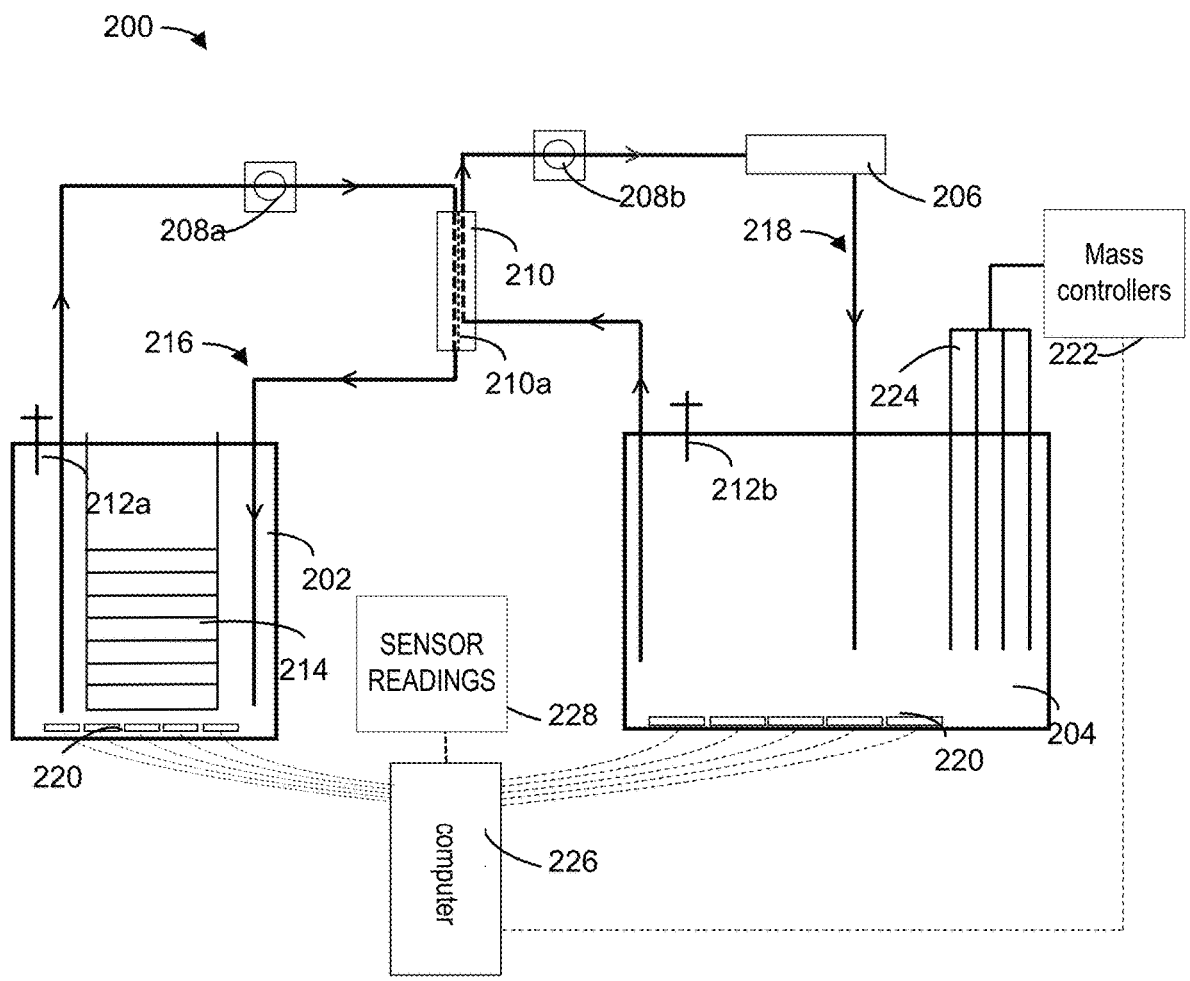
FIG. 10 is a schematic view of a cell culture system according to another embodiment of the present disclosure.

Turning to FIG. 10, an exemplary cell/tissue culture system 200 in accordance to another embodiment of the present invention comprises a bioreactor 202, a fresh medium unit 204, a waste removal unit 206, a plurality of pumps 208 and a dialysis unit 210. Each of the bioreactor 202 and the fresh medium unit 204 may further comprise a port 212a/212b connected to an aseptic connector for venting or sampling purposes. At least one cell culture unit 214 may further be disposed of within the bioreactor 202. The cell culture system 200 further comprises a first circulation 216 and a second circulation 218.

The first fluid circulation 216 connects the bioreactor 202, a first pump 208a and the dialysis unit 210. The first circulation 216 is configured to circulate the first fluid between the bioreactor 202 and the dialysis unit 210. The first pump 208a and/or the tube of the first circulation 216 is configured to create a fluid flow that evenly distributes nutrients inside the bioreactor 202. Such fluid flow is achieved in the absence of a stirrer or agitator in the bioreactor 202. The first fluid may be a cell culture medium which may include a basal medium supplemented with FBS, plant hydrolysates, plant extracts, growth factors or cytokines. Growth factors or cytokines may include but are not limited to, insulin growth factor 1 (IGF-1), insulin, interleukin 6 (IL-6), interleukin 6 receptor (IL-6R), interleukin 11 (IL-11), fibroblast growth factor (FGF), epidermal growth factor (EGF), and transferrin.

The second fluid circulation 218 connects the fresh medium unit 204, the dialysis unit 210, a second pump 208b and the waste removal unit 206. The second circulation 218 is configured to circulate a second fluid among the fresh medium unit 204, the dialysis unit 210 and the waste removal unit 206. The second fluid is dialysate, which may be a fresh basal medium that may include a buffered solution containing components such as, but not limited to, inorganic salts (e.g., calcium chloride (CaCl2)), potassium chloride (KCl), sodium chloride (NaCl), sodium bicarbonate (NaHCO3), sodium dihydrogen phosphate (NaH2PO4), magnesium sulfate (MgSO4), etc.), amino acids, vitamins (e.g., thiamine, riboflavin, folic acid, etc.), and other components such as glucose, beta-mercaptoethanol, ethylenediaminetetraacetic acid (EDTA), and sodium pyruvate.

The cell/tissue culture system 200 may further comprise at least one sensor 220 and at least one mass controller 222 having at least one gas and/or liquid inlet 224 in fluidic connection to the fresh medium unit 204. The gas and/or liquid inlet 224 is configured to intake the gas and/or liquid from the interior of the fresh medium unit 204. The sensor 220 may obtain the temperature, glucose level, glutamine level, carbon dioxide level, ammonia level, pyruvate level, lactate level, pH. The sensor 220 and the mass controller 222 may further be connected to a computer system 226 through a communication network. The computer system 226 may exchange data with the sensor 220 and control the mass controller 222 and the pumps 208 according to parameters that a user directs toward a control application and the data obtained from the sensor 220. The computer system 226 may further connect to a display unit 228 to show the reading of the sensor 220.

In some embodiments, each of the bioreactor 202, fresh medium unit 204, waste removal unit 206 and dialysis unit 210 may be a removable plug-in module. In other words, each of the bioreactor 202, fresh medium unit 204, waste removal unit 206 and dialysis unit 210 is detachably connected to the cell/tissue culture system 200 through an aseptic connector.

In some embodiments, the cell/tissue culture system 200 may include more than one bioreactor 202. In some embodiments, the cell/tissue culture system 200 may include more than one bioreactor 202 with a single set of fresh medium unit 204 and waste removal unit 206. In some embodiments, the size or the volume of the bioreactor 202 may vary. As such, the production of the cell/tissue culture system 200 can be scaled up and down easily.

Specific details of the components of the cell/tissue culture system 200 are set forth below.

The bioreactor 202 is an isolated, stand-alone unit that is physically separated from the fresh medium unit 204 and the waste removal unit 206. Bioreactor 202 may connect to the first fluid circulation 216 through aseptic connectors such that the bioreactor 202 can be detachably connected to the first fluid circulation 216.

The tissue culture holder 214 may be configured to hold the food-grade scaffold which accommodates cell growth on a scaffold or an extracellular matrix which is produced by stem cells grown under a predetermined condition. The cells may grow on the scaffold or extracellular matrix in a three-dimensional environment and form tissue structure. The tissue culture holder 214 may have a plurality of scaffold holders or extracellular matrix holders, each holder may be configured to receive and hold at least one scaffold or extracellular matrix. It may also receive and hold a plurality of scaffolds or extracellular matrix at different thicknesses, which may be stacked in the holder. The tissue culture holder 214 may further comprise a fluid permeable structure to allow fluid in the bioreactor 202 to interact with cells on the scaffold or extracellular matrix from all sides with minimum shear stress. The tissue culture holder 214 may be made of a material that would not be damaged by regular sterilizing methods known in the art, for example, disinfectant agent, ultraviolet light and autoclave. Such material, for example, may be stainless steel, glass or high temperature resistance resin. More than one tissue culture holder 214 may be held in a sterile chamber of the cell culture unit 202, thus allowing easy scale-up according to production demands. For some embodiments, the tissue culture holder 214 may be a supporting tray or porous plate, wherein such tray or plate includes at least one porous which allows medium flow.

The tissue culture holder 214 is configured to optimize the exchange of nutrients and waste between the cells and the culture medium while maintaining the flow of the culture medium at the tissue culture holder 214 to reduce the shear stress acting on the cells, because the developing tissue is not directly perfused, and nutrients are delivered rather by diffusion. Excessive shear stress could kill cells which leads to low yield. The tissue culture holder 214 may further include a holder to hold a scaffold or an extracellular matrix to fix its position in the tissue culture holder 214. The tissue culture holder 214 is optimized such that its vibration is minimized as the culture medium moves around it. It helps the cells to attach to the scaffold or the extracellular matrix firmly, thus enhancing the yield.

In yet some embodiments, the bioreactor 202 does not include culture holder 214, food-grade scaffold and extracellular matrix. The cells in the bioreactor 202 may be in suspension. The bioreactor 202 may further configured to control the shear stress in the bioreactor 202 in order to lower the shear stress acting on the cells. Yet, the bioreactor 202 may include microcarriers such that the cell may culture on it.

The first fluid circulation 216 may include a by-pass to cause the fluid therein to selectively bypass the bioreactor 202 and/or the dialysis unit 210. As such the tissue/cell in the bioreactor 202 may be protected from contamination of the fluid in the first fluid circulation in case there is any malfunction.

Each of the fresh medium unit 204 and the waste removal unit 206 may connect to the second fluid circulation 216 through aseptic connectors such that each of the fresh medium unit 204 and the waste removal unit 206 may be detachably connected to the second fluid circulation 218.

The second fluid circulation 218 may include a by-pass to cause the fluid therein to selectively bypass the fresh medium unit 204, waste removal unit 206 and/or the dialysis unit 210. As such the tissue/cell in the bioreactor 202 may be protected from contamination of the fluid in the first fluid circulation in case there is any malfunction.

In some embodiments, the dialysis unit 210 comprises a dialysis membrane 210a configured to retain desirable macromolecules in the first fluid circulation 216 and allow nutrients of the second fluid in the second fluid circulation 218 such as glucose (180 Da), pyruvate, amino acids, vitamins and minerals to get across the membrane 210a into the first fluid for the replenishment of the nutrients to the cells in the bioreactor 202. As such, the dialysis membrane 210a is configured to retain desirable macromolecules in the bioreactor 202. The desirable macromolecules may also include different kinds of proteins and other macromolecules in the first fluid (both having at least 100 Da), for example, phospholipid (lecithin, ceramide), lipid (DHA, AHA), polysaccharide (glycogen), proteoglycan (heparin, chondroitin), nucleic acid (DNA, RNA), insulin-like growth factor (IGF, 7.5 kDa for a recombinant form) and transforming growth factor-beta (TGF beta, 44 kDa for pro TGF-beta).

Different types of dialysis membrane including Cellulose Ester (CE), Regenerated Cellulose (RC) or Polyvinylidene fluoride (PVDF) may be used. Dialysis membrane 210a of different molecular weight cut-off (MWCO) may be used to retain desirable macromolecules in the first fluid (e.g. growth factors secreted by cells in culture vessel) and allow waste to be removed from the first fluid in the dialysis unit 210. The waste may be growth inhibitors comprising ammonium or lactate. It is observed that ammonium or lactate accumulation can inhibit cell growth and cell productivity. For the dialysis membrane 210a, for example, 100 Da-1,000,000 Da MWCO membrane, preferably 500 Da MWCO membrane, can be used to retain insulin-like growth factor (IGF, 7.5 kDa for a recombinant form) and transforming growth factor-beta (TGF beta, 44 kDa for pro TGF-beta) in the first fluid and allow lactate (89 Da) and ammonia (17 Da) to be removed from the first fluid. Such membrane may also be used to allow nutrients of the second fluid such as glucose (180 Da), pyruvate, amino acids, vitamins and minerals to get across the membrane into the first fluid for replenishment to optimize cell proliferation and/or differentiation. It will be discussed in detail below, the membrane is also configured to retain zeolites, nitrifying bacteria and enzymes in the second fluid. In yet some embodiments, the dialysis unit 210 may be in a form of a hollow fiber cartridge containing semipermeable hollow fibers.

The waste removal unit 206 may comprise biocatalysts or enzymes to reduce or remove growth inhibitors in the second fluid. The waste removal unit 206 may comprise a column of packed-bed zeolite, biocatalyst comprising nitrifying bacteria to reduce or remove ammonia and/or biocatalyst comprising enzymes to reduce or remove lactate by converting lactate into carbon sources.

In some embodiments, the nitrifying bacteria can be incorporated into the waste removal unit 206 in the form of suspension culture. In yet some embodiments, the nitrifying bacteria can also be immobilized in alginate, agarose or gelatin beads, on a membrane, using microparticles or other immobilization methods. Immobilization of microbial cells allows the efficient use of bacterial biocatalysts, which simplifies the separation of bacteria and second fluid and allows the continued use of the biocatalyst. Nitrifying bacteria may be any of the following species: the genera *Nitrosomonas, Nitrosococcus, Nitrobacter, Nitrospina, Nitrospira* or *Nitrococcus*. These bacteria oxidize ammonium or ammonia to nitrite and nitrate.

In some embodiments, enzymes can be used as biocatalysts to convert metabolic waste products (e.g. lactate) into carbon sources that can be used by cells for cell growth, differentiation, and extracellular matrix deposition. In some embodiments, the biocatalyst may be added to the fresh medium unit 204. In some embodiments, the enzyme is lactate dehydrogenase.

In some embodiments, the computer system 222 is a remote computer system. For example, the remote computer system 222 may include a control with software modules that may send and receive signals to/from the sensor 216. The remote computer system 222 may include a microprocessor (not shown) and a computer-readable storage medium or memory (not shown) connected to the microprocessor for storing software and data.

Now, turning to the method of utilizing the cell/tissue culture system 200 for cell production. The method described herein may be used to culture cells such as skin, muscle, adipose and bone cells to produce in vitro meat. The method includes providing the cell/tissue culture system 200 having a bioreactor 202, transfer of metabolic waste and growth inhibitors from the first fluid to the second fluid at the dialysis unit 210, replenishing nutrients to the first fluid from the second fluid at the dialysis unit 210, and removing growth inhibitors and metabolic waste from the second fluid in the waste removal unit 206. As such, the metabolic waste and growth inhibitors in the bioreactor 202 are removed and the nutrients are replenished to the cells in the bioreactor 202 through the dialysis unit 210.

At least one type of cell is added to the bioreactor 202. Suitable types of cells include, but are not limited to, bone, cartilage, muscle, liver, skin, heart, lung and any combinations thereof. Other types of mammalian cells or fish cells may be used within the present invention. Cells from other plant and animal species can be used.

Different types of specialized cells to be expanded in the bioreactor 202 may be obtained by biopsy from live animals. Other starter cells may be stem cells of various origins such as mesenchymal stem cells, induced pluripotent stem cells and satellite cells. The starter cells may also be genetically modified cells or any cell lines.

The cells are grown into tissue in a solid or semi-solid structure mimicking an animal organ, such as a fish organ, by attaching/adhering to a food-grade biocompatible scaffold or extracellular matrix in a sterile chamber or container, such as the bioreactor 202. The food-grade biocompatible scaffold becomes part of the final edible product.

Growth factors and cytokines from fetal bovine serum (FBS) supplements or recombinant sources are introduced into the culture medium (i.e. first fluid in this particular embodiment) in the bioreactor 202 to support cell growth and proliferation. The growth factors and cytokines may include, but are not limited to, insulin growth factor 1 (IGF-1), insulin, interleukin 6 (IL-6), interleukin 6 receptor (IL-6R), interleukin 11 (IL-11), fibroblast growth factor (FGF), epidermal growth factor (EGF), and transferrin. The application may involve co-culturing bioengineered cells with the cultured cells in the bioreactor 202 in the absence of FBS. The bioengineered cells are engineered to secrete the above growth factors and cytokines and supply these biomolecules to the cultured cells as needed for growth and proliferation. The co-culturing method of the present disclosure eliminates the need for animal-derived fetal bovine serum (FBS) in the culture medium. Furthermore, the co-culturing method provides a continuous supply of food-grade specific growth factors and cytokines to the growing isolated cells in situ and simplifies and reduces the cost of the production process. However, in other embodiments, FBS, other serum or proteins from recombinant sources may be used to supply growth factors, cytokines, and other nutrients to support cell growth. In yet some embodiments, the bioreactor 202 could be the bioreactor 30 as shown in FIG. 2 or bioreactor 50 as shown in FIG. 3 or bioreactor 100 as shown in FIG. 4.

In some embodiments, gases may be introduced to optimize cell culture conditions. Nitrogen, oxygen, carbon dioxide or a mixture of gases may be used. The cell culture unit 202 may contain 0-10% of carbon dioxide. The bioreactor 202 may contain 15-30% of oxygen. The bioreactor 202 may contain 60-85% of nitrogen.

In some embodiments, the temperature may be controlled to optimize the cell culture conditions. Different types of cells may have different optimal culture temperatures. The temperature may range from 25-45° C.

In some embodiments, the culture medium in the bioreactor 202 is stirred. The stirring speed in the culture vessel may be optimized to enhance the expansion of cells as it is known that cells react differently to shear stress. Stirring speed may also be optimized to enhance the mixing of inflow culture medium and culture medium inside the cell culture unit 202. Stirring speed may range from 10 rpm-300 rpm.

The pump 208a may circulate the culture medium from the bioreactor 202 to the dialysis unit 210 and back to the bioreactor 202, thereby transferring the culture medium from the bioreactor 202 to the dialysis unit 210.

The fresh basal medium/dialysate containing nutrients for the cells in the bioreactor 202 (i.e. the second fluid in this particular embodiment) is introduced into the fresh medium unit 204 or the second circulation 218. The pump 208b may circulate the fresh basal medium from the fresh medium unit 204 to the dialysis unit 210 and then to the waste removal unit 206. Upon passing through the waste removal unit 206, the fresh basal medium/dialysate returns to the fresh medium unit 204.

Dialysis is performed at dialysis unit 210. For example, lactate, ammonia and other wastes are transferred from the culture medium to the fresh basal medium through the dialysis membrane 210a of the dialysis unit 210 and the nutrients, including glucose and other growth-enhancing compounds, are transferred from the fresh basal medium to the culture medium through the dialysis membrane of the dialysis unit 210. The dialysis membrane 210a of the dialysis unit 210 may also retain desirable macromolecules in the culture medium. The rate of dialysis can be controlled by changing the flowrate of the fresh basal medium into dialysis unit 210, the flowrate of the culture medium into the dialysis unit 210, dialysis membrane's surface area, temperature, and agitation by stirring in the dialysis unit 210. The rate of nutrient replenishment and waste removal of culture medium in dialysis unit 210 may also be controlled by changing pumping speed ranged from 1 ml/min-10 L/min for fluid inflow from the bioreactor 202 into the dialysis unit 210. Similarly, the rate of nutrient replenishment and waste removal of culture medium in dialysis unit 210 may also be controlled by changing pumping speed ranged from 1 ml/min-10 L/min for fluid inflow from the fresh medium unit 204 into the dialysis unit 210.

Metabolic wastes or growth inhibitors move from the culture medium into the fresh basal medium/dialysate inside the dialysis unit 210. Growth inhibitors accumulate in the fresh basal medium/dialysate over time. Basal medium with accumulated growth inhibitors (including but not limited to lactate and ammonia) is then transferred to a waste removal unit 206 by the pump 208b. Metabolic wastes such as ammonia and lactate in the waste medium may be removed by using zeolite as adsorbents. Zeolites are microporous, aluminosilicate minerals. Examples are analcime, chabazite, clinoptilolite, heulandite, natrolite, phillipsite, and stilbite. The waste removal unit 206 may include a column of packed-bed zeolite. The second fluid flows into the waste removal unit 206 from one end, passing through the zeolite and exiting the waste removal unit 206 from another end. The zeolite absorbs toxic chemicals or chemicals inhibiting cell growth in the second fluid, e.g. ammonia and lactate.

In addition to the zeolites or alternatively, nitrifying bacteria may be employed to reduce or remove the ammonia in the second fluid. Since the second fluid circulation 218 is separated from the first fluid circulation 216 and only selected molecules may be exchanged between the first fluid and the second fluid through the membrane, nitrifying bacteria can be used in the cell culture system 200 to remove ammonia. The separation of the first fluid circulation 216 and the second fluid circulation 218 reduces the risk of contamination of the cell culture at the bioreactor 202 by the nitrifying bacteria. Using nitrifying bacteria to remove ammonia directly from the culture medium which has direct contact with the cell culture may contaminate the cell culture.

In addition to the zeolites and/or nitrifying bacteria, or alternatively, biocatalyst may be used to reduce or remove the lactate in the cell culture. Biocatalyst comprising enzymes that can be used to convert metabolic waste products (e.g. lactate) into carbon sources (e.g. pyruvate) that can be used by cells for cell growth, differentiation, and extracellular matrix deposition. In one embodiment, the enzyme is lactate dehydrogenase, which converts lactate into pyruvate. During proliferation, changes in the culture medium (first fluid) are characterized by decreasing pH caused by lactate accumulation. The biocatalyst as described herein helps regulate the pH changes by moving lactate from the culture medium to the fresh basal medium/dialysate and exchanging them in the fresh basal medium/dialysate for fresh carbon sources (e.g. pyruvate) at the dialysis unit 210. The fresh carbon source can then be transferred to the culture medium to further sustainable growth and development of the tissue.

Using biocatalyst to remove lactate offers a lot of benefits. Adding carbon sources like glucose is expensive, invasive to the culture and can be prone to human and mechanical error. Therefore, by converting metabolic waste products into carbon sources that cells can use for proliferation, differentiation, and extracellular matrix deposition, the cost for the production can be decreased and the efficiency for the production can be increased.

Pyruvate metabolism has been demonstrated to generate lower concentrations of deleterious ammonia and reduced $pCO_2$. Therefore, by lowering the lactate concentration in the culture through the dialysis unit 210, boasting pyruvate metabolism resulting in decreased ammonia production and lower $pCO_2$.

The removal of ammonia and lactate using nitrifying bacteria and biocatalyst under this embodiment may be applied to the cell/tissue culture system 200. In particular, the nitrifying bacteria and the biocatalyst may also be incorporated into the waste removal unit 206.

As shown above, the present invention also keeps nutrients such as glucose at an optimal level and growth inhibitors such as ammonia and lactate at a minimal level for optimal cell viability and cell growth.

The present invention also shows that the use of enzymatic conversions of metabolic waste products into fresh carbon sources that can promote cell growth, differentiation, and extracellular matrix deposition. This reduces the costs of the culture medium and the production process.

In addition, the present invention enhances the cell expansion process and reduces the production costs of the in vitro meat industry and tissue engineering by retaining growth factors secreted by cells and reducing the use of animal-derived serum in the culture medium. The present invention can be used for large-scale meat production.

The in vitro meat production method of the present disclosure provides meat products with a simple tissue organization of one cell type. The meat product with one cell type is easier to make, develop, and commercialize compared to other cultured meats having multiple cell types. Alternative embodiments of the present disclosure provide meat products with tissue organization of multiple cell types. Bio-engineered cells are co-cultured with the growing animal cells to supply the growing fish cells with food-grade growth factors and cytokines for cell growth and proliferation in situ, reducing or eliminating the need for animal-derived FBS in the culture medium. The co-culturing technique simplifies the production process and reduces production costs.

Furthermore, the nutrients of the in vitro meat product may be customized to generate a healthier food product. For example, the in vitro meat product may be customized according to diet recommendations from a dietician or a personal genomic test. Healthy nutrients such as high-density cholesterol, polyunsaturated fatty acids, and mono-unsaturated fatty acids in the meat product may be enriched by culturing the cells in specific conditions. Alternatively, or in combination with this, nutrients known to be damaging to health such as low-density cholesterol and saturated fatty acids may be reduced by culturing the cells in specific conditions. Micronutrients, such as vitamins and minerals, may also be enhanced. Nutrient customization of the in vitro meat products may be achieved in various ways such as, but not limited to, 1) tailoring the nutrients fed to the growing cells during cell culture, and/or 2) controlling the proportions of layering scaffolds or extracellular matrix with different cells.

The production of the in vitro food product is under a clean, sterile and highly controlled process. Thus, undesirable degradation by microorganisms such as bacterial or fungi of the nutrients in the food product is minimized. Undesirable taste and smell from the breakdown of nutrients by microorganisms are also minimized. This property of cultivated food enables new uses in cooking and helps creates novel recipes. One such application of in vitro food is in vitro fish maw derived from fish swim bladders. Conventional fish maw has an undesirable fishy taste and smell due to the degradation of amine by bacteria in the production process. This undesirable property limits the food ingredient to savory dishes served hot or warm. In vitro fish maw produced from cell culture technology does not have an undesirable fishy taste and smell. In addition to hot and savory dishes, in vitro fish maw can be used in sweet dishes, as a dessert or in a ready-to-eat format served at chilled or at ambient temperature.

What is claimed is:

1. A system for in vitro meat production comprising:
    at least one bioreactor, wherein the at least one bioreactor comprises a sterile bioreactor configured to hold a fluid and at least one type of cells to form tissue, wherein the sterile bioreactor comprises a second solid phase support separated from a first solid phase support by a mesh, wherein the second solid phase support is configured to contain bioengineered cells configured to secrete nutrients, growth factors, and cytokines for bioengineered cells growing on the second solid phase support in situ, wherein the second solid phase support is further configured to physically separate the bioengineered cells from at least one type of cells on the first solid phase support;
    a dialysis device comprising a dialysis membrane configured to replenish nutrients to the cells and remove metabolic waste from the sterile bioreactor to dialysate;
    a fresh medium device connected to the dialysis unit device and configured to supply the dialysate to the dialysis device; and
    a waste removal device connected to the fresh medium device and configured to remove the metabolic waste from the dialysate, wherein the waste removal device is physically separated from the sterile bioreactor and the fresh medium device;
    wherein the dialysate comprises nutrients for the cells,
    wherein the metabolic waste comprises ammonia and lactate,
    wherein the waste removal device comprises a first biocatalyst configured to breakdown ammonia,
    wherein the waste removal device comprises a second biocatalyst configured to breakdown lactate to pyruvate, thereby generating fresh carbon sources to promote cell growth in the sterile bioreactor,
    wherein the sterile bioreactor, the dialysis device, the fresh medium device and the waste removal device are detachably connected to each other and connected to the system via aseptic connectors.

2. The system of claim 1, wherein the second biocatalyst is an enzyme configured to break down lactate.

3. The system of claim 1, wherein the first biocatalyst is nitrifying bacteria.

4. The system of claim 1, wherein the dialysis membrane is at least one 500 Daltons (Da) molecular weight cut-off (MWCO) membrane, wherein the membrane is selected from Cellulose Ester (CE), Regenerated Cellulose (RC), and Polyvinylidene fluoride (PVDF).

5. The system of claim 4, wherein dialysis membrane is configured to retain macromolecules in the sterile bioreactor, wherein the macromolecules comprise one or more of the following: proteins having a molecular weight of at least 100 Da, phospholipids, lipids, polysaccharides, proteoglycans, nucleic acids, insulin-like growth factor and transforming growth factor-beta.

6. The system of claim 1, wherein the at least one bioreactor comprises a second bioreactor, wherein the sterile bioreactor and the second bioreactor are connected in parallel.

7. The system of claim 1, wherein the sterile bioreactor further comprises
    one or more platforms for cells to grow three-dimensionally thereon, wherein each of the one or more platforms is an edible scaffold or extracellular matrix; and
    a holder configured to receive and hold said one or more platforms.

8. The system of claim 1, wherein the sterile bioreactor is configured to support cell growth in suspension or on microcarriers on the first solid phase support, the second solid phase support, or both.

9. The system of claim 1, further comprising a pump and a tube connected to the sterile bioreactor, wherein the pump is configured to create a fluid flow that evenly distributes nutrients in the fluid inside the sterile bioreactor in the absence of a stirrer or agitator in the system.

* * * * *